(12) United States Patent
Swanson et al.

(10) Patent No.: US 6,514,246 B1
(45) Date of Patent: *Feb. 4, 2003

(54) SYSTEMS AND METHODS FOR FORMING LARGE LESIONS IN BODY TISSUE USING CURVILINEAR ELECTRODE ELEMENTS

(75) Inventors: David K. Swanson, Mountain View, CA (US); Thomas Bourne, Mountain View, CA (US); Sidney D. Fleischman, Menlo Park, CA (US)

(73) Assignee: EP Technologies, Inc., San Jose, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/111,308

(22) Filed: Jul. 7, 1998

Related U.S. Application Data

(63) Continuation of application No. 08/772,065, filed on Dec. 9, 1996, now Pat. No. 6,171,306, which is a continuation of application No. 08/287,310, filed on Aug. 8, 1994, now Pat. No. 5,582,609, which is a continuation-in-part of application No. 08/138,142, filed on Oct. 15, 1993, now abandoned, which is a continuation-in-part of application No. 08/136,680, filed on Oct. 15, 1993, now abandoned, which is a continuation-in-part of application No. 08/137,576, filed on Oct. 15, 1993, now abandoned, which is a continuation-in-part of application No. 08/138,235, filed on Oct. 15, 1993, now abandoned, which is a continuation-in-part of application No. 08/138,452, filed on Oct. 15, 1993, now abandoned.

(51) Int. Cl.[7] ................................................ A61B 18/18

(52) U.S. Cl. ........................................ 606/41; 600/374

(58) Field of Search .................... 606/41, 42, 45–50; 607/101, 102, 115, 116, 122; 600/372, 374

(56) References Cited

U.S. PATENT DOCUMENTS

| 2,245,880 A | 6/1941 | Tipton |
| 3,230,957 A | 1/1966 | Seifert |
| 3,769,984 A | 11/1973 | Muench |
| 4,481,953 A | 11/1984 | Gold et al. |
| 4,522,212 A | 6/1985 | Gelinas et al. |
| 4,532,924 A | 8/1985 | Auth et al. |
| 4,641,649 A | 2/1987 | Walinsky et al. |
| 4,643,186 A | 2/1987 | Rosen et al. |
| 4,660,571 A | 4/1987 | Hess et al. |
| 4,677,990 A | 7/1987 | Neubauer |
| 4,699,147 A | 10/1987 | Chilson et al. |

(List continued on next page.)

FOREIGN PATENT DOCUMENTS

| EP | 0 317 489 | 5/1989 |
| WO | WO89/06148 | 7/1989 |
| WO | WO93/04734 | 3/1993 |

OTHER PUBLICATIONS

"Intracardiac Echocardiography Radiofrequency Catheter Ablation of Cardiac Arrhythmias," Chu et al., *NASPE*, Apr. 1993.

(List continued on next page.)

*Primary Examiner*—Michael Peffley
(74) *Attorney, Agent, or Firm*—Henricks, Slavin & Holmes LLP

(57) ABSTRACT

Systems and associated methods form larger and deeper lesion patterns by shaping a support body with multiple electrodes in ways that increase the density of the electrodes per given tissue area. The support body can carry either elongated, continuous electrodes or arrays of non-contiguous, segmented electrodes.

11 Claims, 15 Drawing Sheets

U.S. PATENT DOCUMENTS

| | | |
|---|---|---|
| 4,724,836 A | 2/1988 | Okada |
| 4,759,378 A | 7/1988 | Swendson et al. |
| 4,765,331 A | 8/1988 | Petruzzi et al. |
| 4,860,769 A | 8/1989 | Fogarty et al. |
| 4,892,102 A | 1/1990 | Astrinsky |
| 4,913,142 A | 4/1990 | Kittrell et al. |
| 4,934,049 A | 6/1990 | Kiekhafer |
| 4,940,064 A | 7/1990 | Desai |
| 5,016,808 A | 5/1991 | Heil |
| 5,026,959 A | 6/1991 | Ito et al. |
| 5,057,106 A | 10/1991 | Kasevich et al. |
| 5,078,716 A | 1/1992 | Doll |
| 5,101,836 A | 4/1992 | Lee |
| 5,117,828 A | 6/1992 | Metzger et al. |
| 5,150,717 A | 9/1992 | Rosen et al. |
| 5,156,151 A | 10/1992 | Imran |
| 5,186,171 A | 2/1993 | Kuhry |
| 5,192,280 A | 3/1993 | Parins |
| 5,197,963 A | 3/1993 | Parins |
| 5,215,103 A | 6/1993 | Desai |
| 5,228,442 A | 7/1993 | Imran |
| 5,237,996 A | 8/1993 | Waldman et al. |
| 5,239,999 A | 8/1993 | Imran |
| 5,242,441 A | 9/1993 | Avitall |
| 5,255,679 A | 10/1993 | Imran |
| 5,263,493 A * | 11/1993 | Avitall ..................... 607/122 |
| 5,265,623 A | 11/1993 | Kroll et al. |
| 5,275,162 A | 1/1994 | Edwards et al. |
| 5,281,218 A | 1/1994 | Imran |
| 5,290,286 A | 3/1994 | Parins |
| 5,293,868 A | 3/1994 | Nardella |
| 5,293,869 A | 3/1994 | Edwards et al. |
| 5,311,866 A | 5/1994 | Kagen et al. |
| 5,313,943 A | 5/1994 | Houser et al. |
| 5,322,064 A | 6/1994 | Lundquist |
| 5,324,284 A | 6/1994 | Imran |
| 5,327,889 A | 7/1994 | Imran |
| 5,327,905 A * | 7/1994 | Avitall ..................... 607/122 |
| 5,328,467 A | 7/1994 | Edwards et al. |
| 5,334,193 A | 8/1994 | Nardella |
| 5,341,807 A | 8/1994 | Nardella |
| 5,345,936 A | 9/1994 | Pomeranz et al. |
| 5,348,554 A | 9/1994 | Imran et al. |
| 5,354,297 A | 10/1994 | Avitall |
| 5,357,956 A | 10/1994 | Nardella |
| 5,358,478 A | 10/1994 | Thompson |
| 5,365,926 A | 11/1994 | Desai |
| 5,366,443 A | 11/1994 | Eggers et al. |
| 5,370,644 A | 12/1994 | Langberg |
| 5,370,678 A | 12/1994 | Edwards et al. |
| 5,383,874 A | 1/1995 | Jackson et al. |
| 5,383,917 A | 1/1995 | Desai et al. |
| 5,397,341 A | 3/1995 | Hirschberg |
| 5,403,311 A | 4/1995 | Abele |
| 5,405,346 A | 4/1995 | Grundy et al. |
| 5,411,025 A | 5/1995 | Webster, Jr. |
| 5,433,198 A | 7/1995 | Desai et al. |
| 5,454,370 A | 10/1995 | Avitall |
| 5,472,441 A | 12/1995 | Edwards |
| 5,487,385 A | 1/1996 | Avitall |
| 5,500,012 A | 3/1996 | Brucker et al. |
| 5,545,193 A | 8/1996 | Fleischman et al. |
| 5,549,661 A | 8/1996 | Kordis et al. |
| 5,573,553 A | 11/1996 | Struhl |
| 5,575,819 A | 11/1996 | Swanson et al. |
| 5,582,609 A | 12/1996 | Swanson et al. |
| 5,607,422 A | 3/1997 | Smeets |
| 5,626,136 A | 5/1997 | Webster |
| 5,651,780 A | 7/1997 | Jackson et al. |
| 5,673,695 A | 10/1997 | McGee |
| 5,800,428 A | 9/1998 | Nelson |
| 5,800,482 A | 9/1998 | Pomeranz |
| 5,871,523 A | 2/1999 | Fleischman et al. |
| 6,001,093 A | 12/1999 | Swanson et al. |
| 6,106,522 A | 8/2000 | Fleischman et al. |
| 6,129,724 A | 10/2000 | Fleischman et al. |
| 6,146,379 A | 11/2000 | Fleischman et al. |
| 6,171,306 B1 | 1/2001 | Swanson et al. |
| 6,241,754 B1 | 6/2001 | Swanson et al. |

OTHER PUBLICATIONS

"Delivery of Radiofrequency Energy to All Four Poles of a Catheter Increases Lesion Size," Sean C. Mackey et al., Oct. 1992, p. 3119.

"Observations on Electrode–Tissue Interface Temperature and Effect on Electrical Impedance During Radiofrequency Ablation of Ventricular Myocardium," Haines, et al., *Circulation*, Sep. 1990, pp. 1034–1038.

"Catheter Ablation of the Atrioventricular Junction with Radiofrequency Energy," Jonathan J. Langberg M.D. et al., *Circulation*, Dec. 1989, vol. 80 No. 6, pp. 1527–1535.

"Atrial Flutter—Update on the Mechanism and Treatment," Olshanky et al., *PACE*, Dec. 1992.

"Radiofrequency Ablation of the Inferior Vena Cava–Tricuspid Valve Isthmus in Common Atrial Flutter" (Abstract), Cosio et al., *AM J Cardio*, Mar. 1993.

"Efficacy of Radiofrequency Ablation of Atrial of Tissue in Common Atrial Flutter," Kirkorian et al., *NASPE*, May 1993.

"Radiofrequency Catheter Ablation of Atrial Arrhythmias Results and Mechanisms," Michael D. Lesh M.D., *Circulation*, Mar. 1994, vol. 89 No. 3, pp. 1974–1089.

"Catheter Ablation of Atrial Flutter Using Radio Frequency Energy," (Abstract) Hugh Calkins et al., *Circulation*, Oct. 1992.

"Radiofrequency Catheter Ablation for the Treatment of Human Type 1 Atrial Flutter. Identification of a Critical Zone in the Reentrant Circuit By Endocardial Mapping Techniques," (Abstract), Feld et al., *Circulation*, Oct. 1992, pp. 1233–1240.

"Radiofrequency Catheter Ablation of Common Type Atrial Flutter," Nakagawa et al., *NASPE*, May 1993.

"Catheter Ablation of Atrial Flutter Circuits" (Abstract), Cosio et al., *PACE*, Mar. 1993.

"Radiofrequency Current Delivery by Way of BiPolar Tricuspid Annulus–mitral Annulus Electrode Configuration for Ablation of Posteroseptal Accessory Pathways," (Abstract), Bashir et al., *J. Am. Coll. Cardiol.*, Aug. 1993.

"Electrotherapy of Supraventricular Tachycardia" (Abstract), Hoffman, et al., *Z. Gesamte Inn Med.*, Sep. 1993.

"Radiofrequency Catheter Ablation for Management of Cardiac Tachyarrhythmias" (Abstract), Wood et al., *AM. J. Med. Sci.*, Oct. 1993.

"Atrial Fibrillation and Atrial Flutter" (Abstract), Geraets et al., *Clin. Pharm.*, Oct. 1993.

U.S. patent application Ser. No. 08/529,354 and a copy of the claims pending as of May 6, 2002.

U.S. patent application Ser. No. 09/579,703 and a copy of the claims pending as of May 6, 2002.

U.S. patent application Ser. No. 09/460,296 and a copy of the claims pending as of May 6, 2002.

U.S. patent application Ser. No. 09/505,354 and a copy of the claims pending as of May 6, 2002.

U.S. patent application Ser. No. 09/870,288 and a copy of the claims pending as of May 6, 2002.

\* cited by examiner

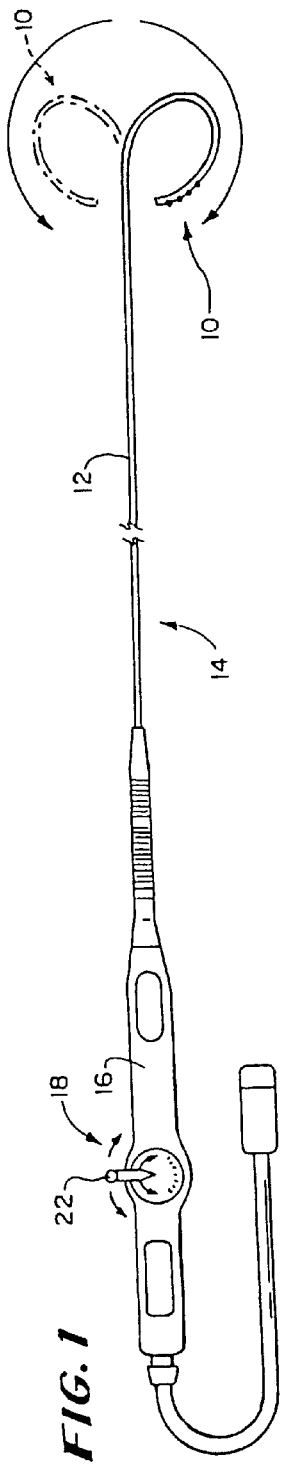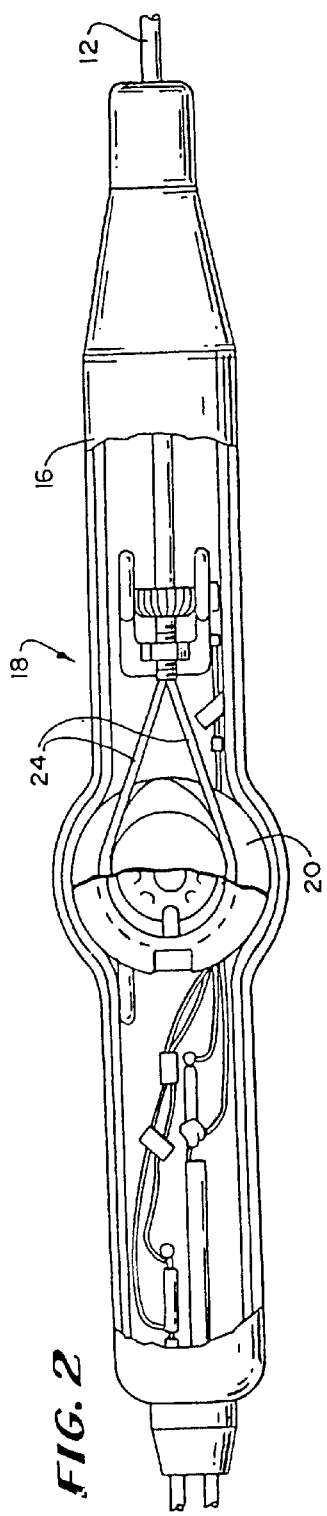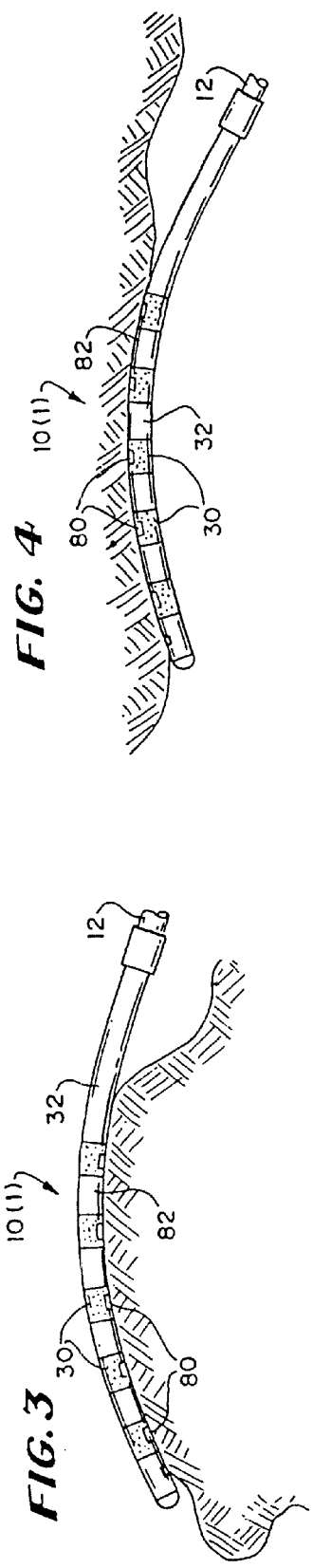

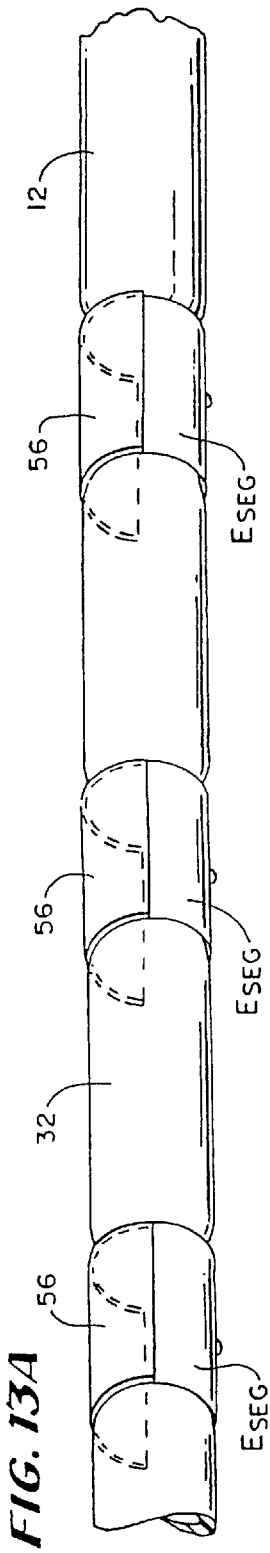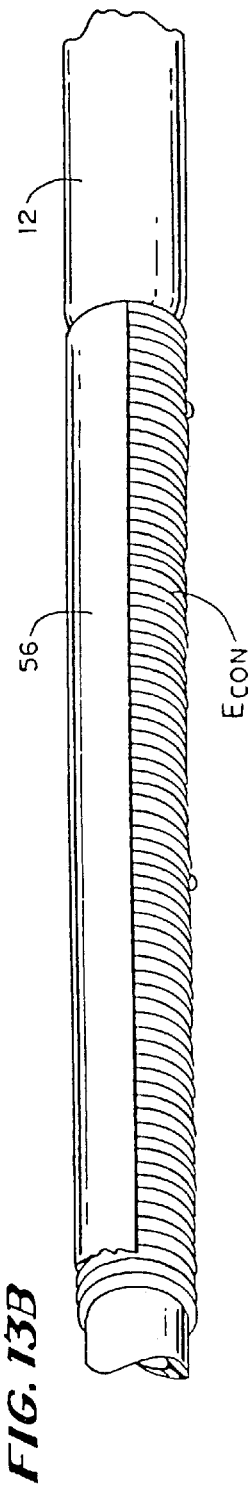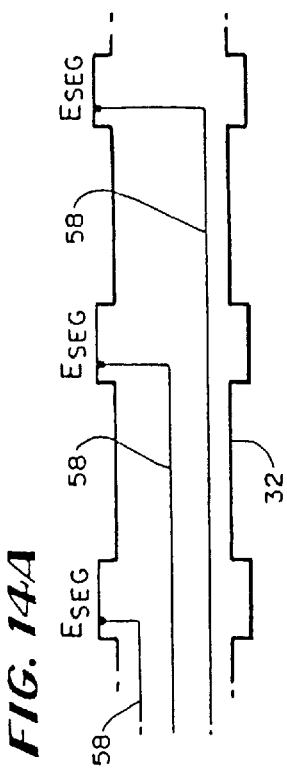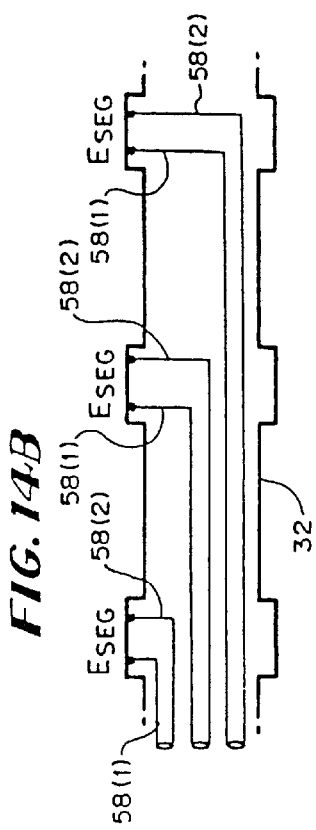

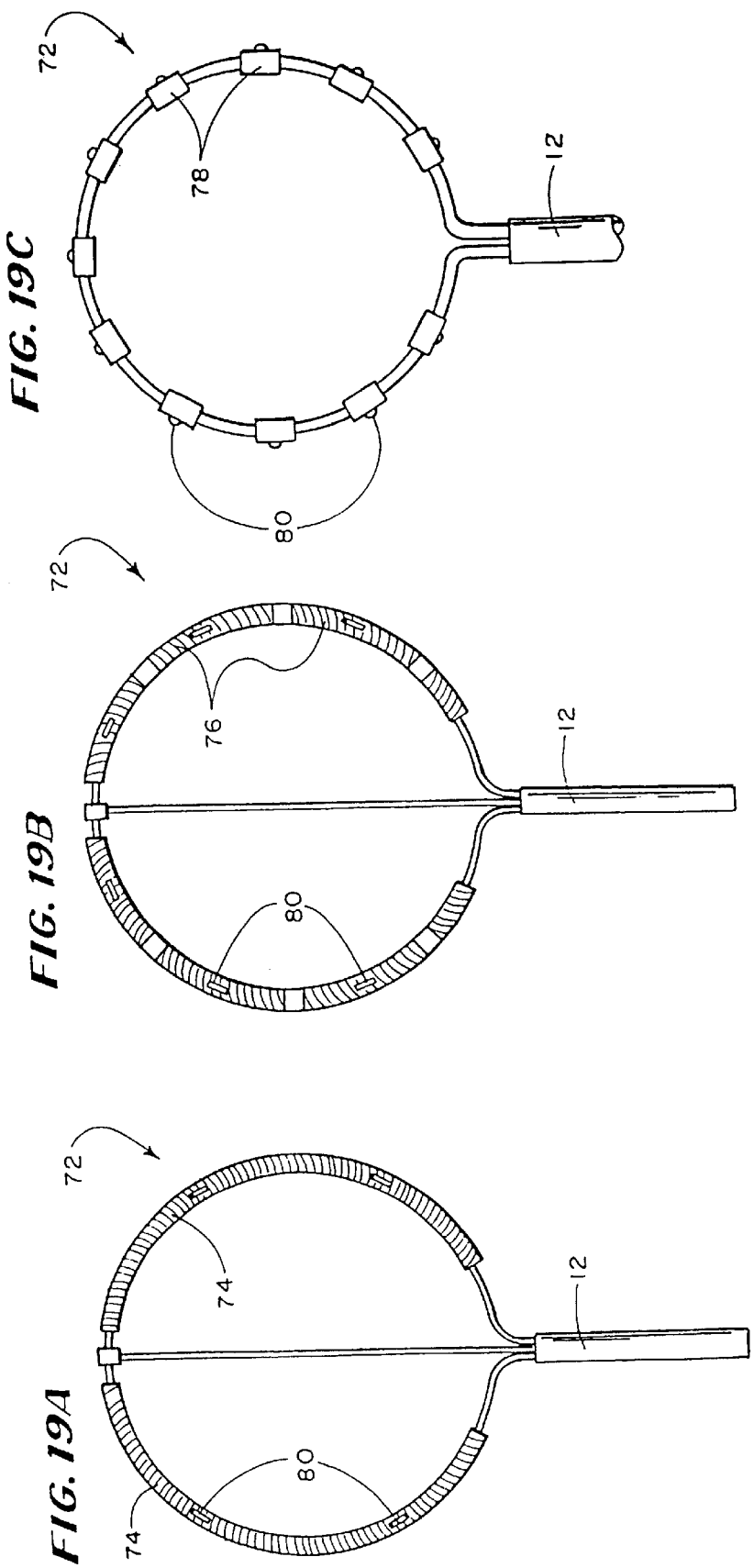

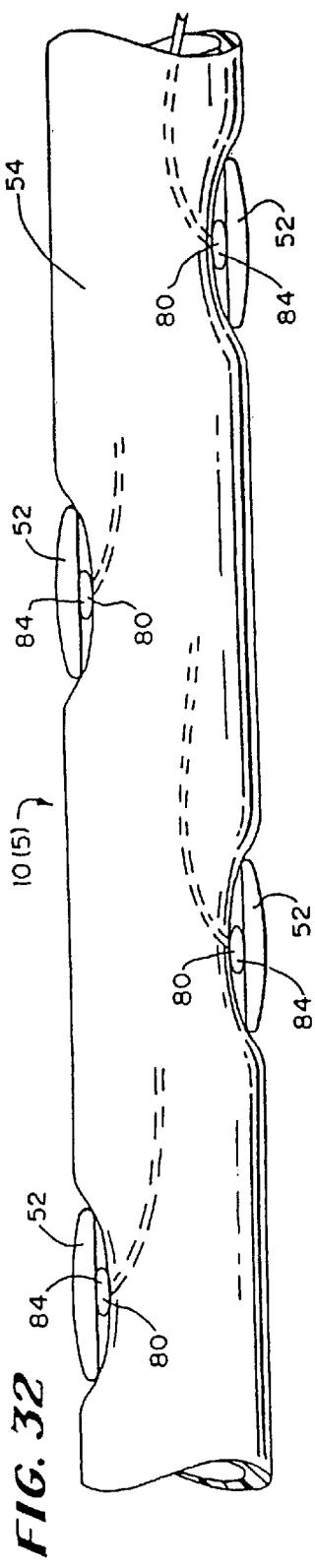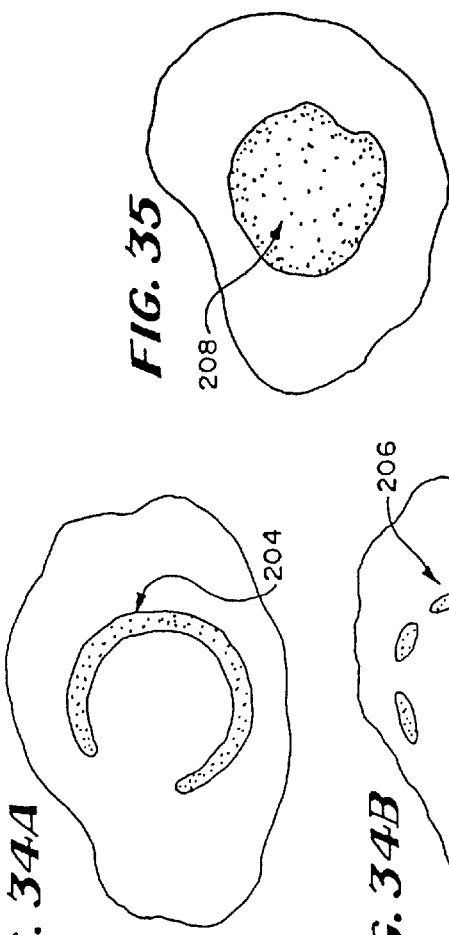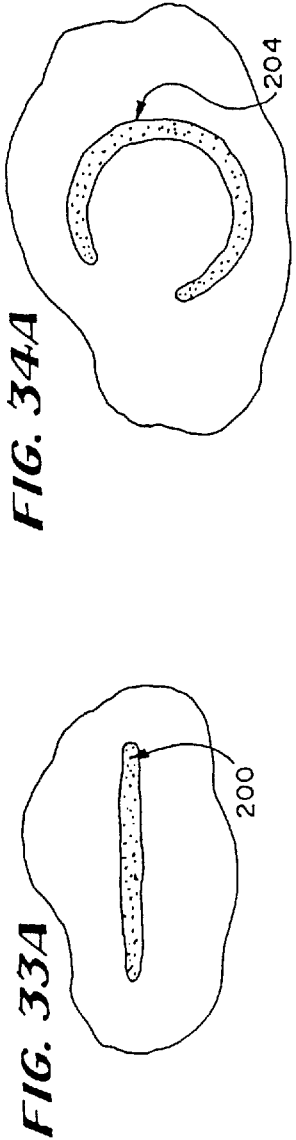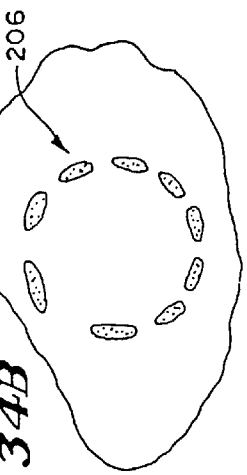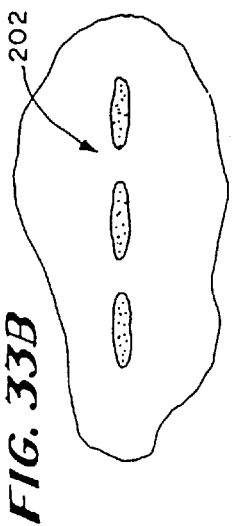

SYSTEMS AND METHODS FOR FORMING LARGE LESIONS IN BODY TISSUE USING CURVILINEAR ELECTRODE ELEMENTS

CROSS-REFERENCE TO RELATED APPLICATION

This application is a continuation of application Ser. No. 08/772,065, filed Dec. 9, 1996, now U.S. Pat. No. 6,171,306 which is a continuation of application Ser. No. 08/287,310, filed on Aug. 8, 1994, now U.S. Pat. No. 5,582,609, which is a continuation-in-part of application Ser. No. 08/138,142, filed on Oct. 15, 1993, now abandoned, and a continuation-in-part of application Ser. No. 08/136,680, filed Oct. 15, 1993, now abandoned, and a continuation-in-part of application Ser. No. 08/137,576, filed Oct. 15, 1993, now abandoned, and a continuation-in-part of application Ser. No. 08/138,235, filed Oct. 15, 1993, now abandoned, and a continuation-in-part of application Ser. No. 08/138,452, filed Oct. 15, 1993, now abandoned.

FIELD OF THE INVENTION

The invention relates to systems and methods for ablating myocardial tissue for the treatment of cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

For example, in electrophysiological therapy, ablation is used to treat cardiac rhythm disturbances.

During these procedures, a physician steers a catheter through a main vein or artery into the interior region of the heart that is to be treated. The physician places an ablating element carried on the catheter near the cardiac tissue that is to be ablated. The physician directs energy from the ablating element to ablate the tissue and form a lesion.

In electrophysiological therapy, there is a growing need for ablating elements capable of providing lesions in heart tissue having different geometries.

For example, it is believed the treatment of atrial fibrillation requires the formation of long, thin lesions of different curvilinear shapes in heart tissue. Such long, thin lesion patterns require the deployment within the heart of flexible ablating elements having multiple ablating regions. The formation of these lesions by ablation can provide the same therapeutic benefits that the complex suture patterns that the surgical maze procedure presently provides, but without invasive, open heart surgery.

As another example, it is believed that the treatment of atrial flutter and ventricular tachycardia requires the formation of relatively large and deep lesions patterns in heart tissue. Merely providing "bigger" electrodes does not meet this need. Catheters carrying large electrodes are difficult to introduce into the heart and difficult to deploy in intimate contact with heart tissue. However, by distributing the larger ablating mass required for these electrodes among separate, multiple electrodes spaced apart along a flexible body, these difficulties can be overcome.

With larger and/or longer multiple electrode elements comes the demand for more precise control of the ablating process. The delivery of ablating energy must be governed to avoid incidences of tissue damage and coagulum formation. The delivery of ablating energy must also be carefully controlled to assure the formation of uniform and continuous lesions, without hot spots and gaps forming in the ablated tissue.

SUMMARY OF THE INVENTION

A principal objective of the invention is to provide improved systems and methodologies to form larger and deeper lesions using curvilinear ablating elements.

One aspect of the invention provides a device and associated method for creating large lesion patterns in body tissue. The device and method use a support element having a curved region to peripherally contact a tissue area. The support element carries at least two energy emitting zones on the curved region, which are mutually separated across the contacted tissue area. The mutual separation between the zones across the contacted tissue area is sufficient to create, when the zones simultaneously emit energy, an additive heating effect to form a continuous lesion pattern in the contacted tissue area that spans across the contacted tissue area.

In one embodiment, a continuous energy emitting electrode is present on the curved region of the support element.

In another embodiment, the two energy emitting zones comprise non-contiguous energy emitting segments on the curved region mutually separated across the contacted tissue area.

Another aspect of the invention provides a device and associated method for ablating body tissue using a support element having a region curved along a preselected radius to peripherally contact a tissue area. The device and method include at least two energy emitting zones on the curved region, which are mutually separated across the contacted tissue area. The radius of curvature of the curved region is equal to or less than about 3.5 times the smaller of the diameters of the first and second zones. When the zones are conditioned to simultaneously emit energy, a continuous large lesion forms that spans across the contacted tissue area.

In one embodiment implementing this aspect of the invention, the device and method employ a continuous energy emitting electrode on the curved region of the support element.

In another embodiment that implements this aspect of the invention, the two energy emitting zones comprise non-contiguous electrode segments separated on the curved region of the support element. In a preferred embodiment, the length of each zone is greater than about 5 times the diameter of the respective zone.

Another aspect of the invention provides a device and associated method for ablating body tissue that also use a curved support element that peripherally contact a tissue area. The device and method include at least two non-contiguous energy emitting zones on the curved region, which are mutually separated across the contacted tissue area.

According to this aspect of the invention, the separation between the zones across the contacted tissue area is equal to or less than about 7 times the smaller of the diameters of the first and second zones. When the zones are conditioned to simultaneously emit energy, a continuous large lesion is formed spanning across the contacted tissue area.

In one embodiment implementing this aspect of the invention, the device and method employ a continuous energy emitting electrode on the curved region of the support element.

In another embodiment that implements this aspect of the invention, the two energy emitting zones comprise non-contiguous electrode segments separated on the curved region of the support element. In a preferred embodiment of this aspect of the invention, the length of each zone is equal to or less than about 5 times the diameter of the respective zone.

Other features and advantages of the inventions are set forth in the following Description and Drawings, as well as in the appended Claims.

BRIEF DESCRIPTION OF THE DRAWINGS

FIG. 1 is a view of a probe that carries a flexible ablating element having multiple temperature sensing elements;

FIG. 2 is an enlarged view of the handle of the probe shown in FIG. 1, with portions broken away and in section, showing the steering mechanism for flexing the ablating element;

FIGS. 3 and 4 show the flexure of the ablating element against different tissue surface contours;

FIGS. 13A/B are side views of, respectively, segmented electrode elements and a continuous electrode element which have been masked on one side with an electrically and thermally insulating material;

FIGS. 14A/B are schematic views of electrically connecting electrode segments to, respectively, single and multiple wires;

FIGS. 19A/B/C are views of a generally hoop-shaped multiple electrode structure for making lesions that span across diagonally and/or diametric spaced electrode regions;

FIG. 32 is a view of a flexible ablating element comprising a continuous wrapped ribbon, showing a manner of mounting temperature sensing elements along the length of the ribbon;

FIG. 33A is a top view of an elongated lesion pattern that is generally straight and continuous, which non-contiguous energy emitting zones form, when conditioned to simultaneous transmit energy to an indifferent electrode, provided that they are spaced sufficiently close to each other to generate additive heating effects;

FIG. 33B is a top view of an elongated lesion pattern that is generally straight and segmented, which non-contiguous energy emitting zones form when they are not spaced sufficiently close to each other to generate additive heating effects;

FIG. 34A is a top view of an elongated, curvilinear lesion pattern that is continuous, which non-contiguous energy emitting zones create when they are sufficiently close to each other along the periphery of a curvilinear path generate additive heating effects between them when they simultaneously emit energy, but when they are otherwise positioned far enough apart across from each other to not generate additive heating effects that span across the curvilinear path;

FIG. 34B is a top view of an elongated, curvilinear lesion pattern that is segmented or interrupted, which non-contiguous energy emitting zones create when they are not sufficiently adjacent to each other either along or across the periphery of a curvilinear path to generate additive heating effects between them; and FIG. 35 is is a top view of a large lesion pattern that spans across a curvilinear path, which non-contiguous energy emitting zones create when they are sufficiently adjacent to each other to generate additive heating effects across the periphery of the curvilinear path.

Figures 5, 6:
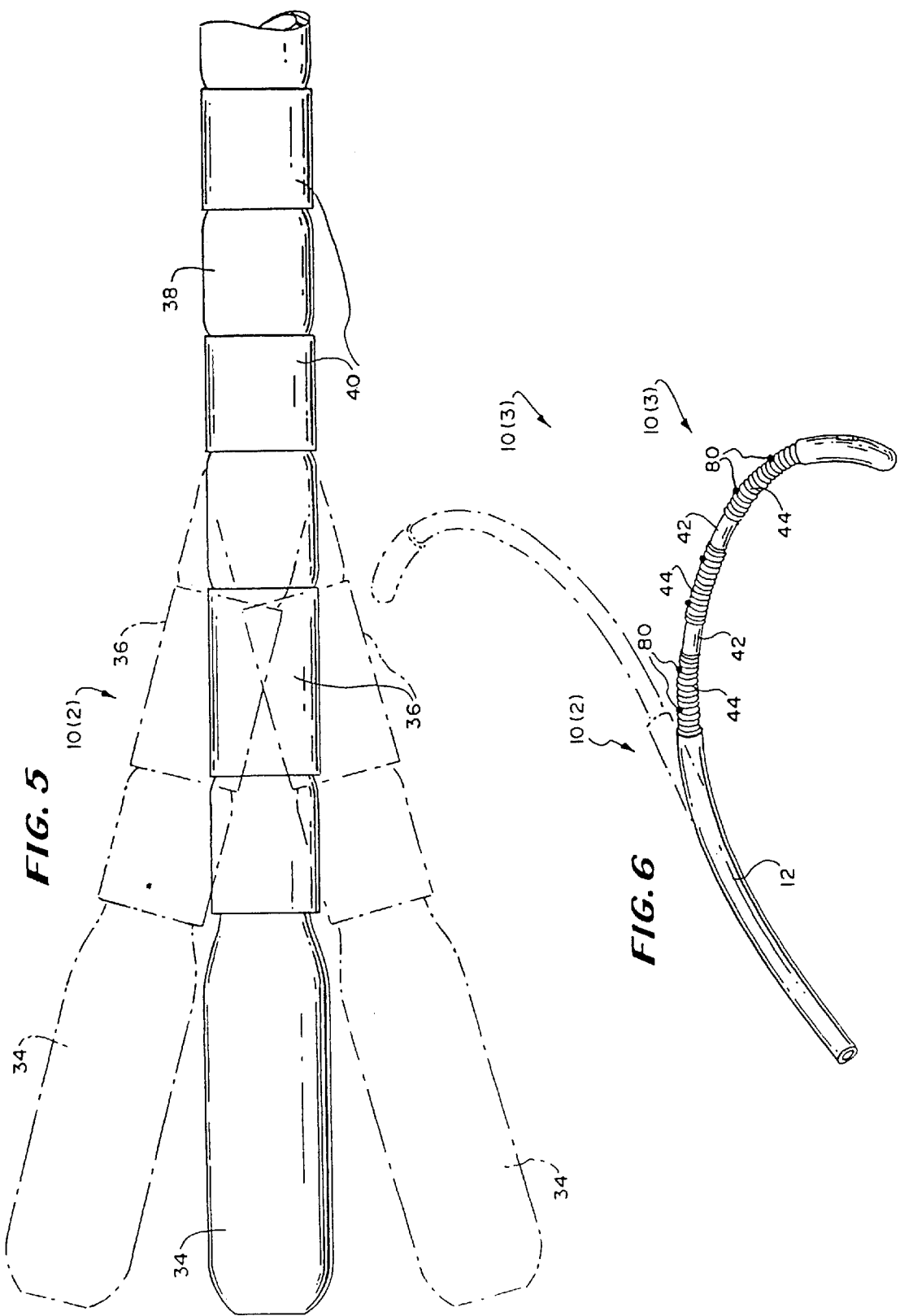
FIG. 5 is a side view of a flexible ablating element comprising a rigid tip electrode element and a rigid body electrode segment.
FIG. 6 is a perspective view of a segmented flexible electrode element, in which each electrode segment comprises a wrapped wire coil.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

This Specification discloses multiple electrode structures that embody aspects the invention. This Specification also discloses tissue ablation systems and techniques using multiple temperature sensing elements that embody other aspects of the invention. The illustrated and preferred embodiments discuss these structures, systems, and techniques in the context of catheter-based cardiac ablation. That is because these structures, systems, and techniques are well suited for use in the field of cardiac ablation.

Still, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

I. Flexible Ablating Elements

FIG. 1 shows a flexible ablating element 10 for making lesions within the heart.

The element 10 is carried at the distal end of a catheter body 12 of an ablating probe 14. The ablating probe 14 includes a handle 16 at the proximal end of the catheter body 12. The handle 16 and catheter body 12 carry a steering mechanism 18 for selectively bending or flexing the ablating element 10 in two opposite directions, as the arrows in FIG. 1 show.

The steering mechanism 18 can vary. In the illustrated embodiment (see FIG. 2), the steering mechanism 18 includes a rotating cam wheel 20 with an external steering lever 22 (see FIG. 1). As FIG. 2 shows, the cam wheel 20 holds the proximal ends of right and left steering wires 24. The wires 24 pass through the catheter body 12 and connect to the left and right sides of a resilient bendable wire or spring 26 (best shown in FIGS. 20 and 23) enclosed within a tube 28 inside the ablating element 10.

Further details of this and other types of steering mechanisms for the ablating element 10 are shown in Lundquist and Thompson U.S. Pat. No. 5,254,088, which is incorporated into this Specification by reference.

As FIG. 1 shows, forward movement of the steering lever 22 flexes or curves the ablating element 10 down. Rearward movement of the steering lever 22 flexes or curves the ablating element 10 up.

Various access techniques can be used to introduce the probe 14 into the desired region of the heart. For example, to enter the right atrium, the physician can direct the probe 14 through a conventional vascular introducer through the femoral vein. For entry into the left atrium, the physician can direct the probe 14 through a conventional vascular introducer retrograde through the aortic and mitral valves.

Alternatively, the physician can use the delivery system shown in pending U.S. application Ser. No. 08/033,641, filed Mar. 16, 1993, and entitled "Systems and Methods Using Guide Sheaths for Introducing, Deploying, and Stabilizing Cardiac Mapping and Ablation Probes."

The physician can verify intimate contact between the element 10 and heart tissue using conventional pacing and sensing techniques. Once the physician establishes intimate contact with tissue in the desired heart region, the physician applies ablating energy to the element 10. The type of ablating energy delivered to the element 10 can vary. In the illustrated and preferred embodiment, the element 10 emits electromagnetic radio frequency energy.

The flexible ablating element 10 can be configured in various ways. With these different configurations, the flexible ablating element can form lesions of different characteristics, from long and thin to large and deep in shape.

A. Segmented, Rigid Electrode Element.

FIGS. 3 and 4 show one implementation of a preferred type of flexible ablating element, designated 10(1). The element 10(1) includes multiple, generally rigid electrode elements 30 arranged in a spaced apart, segmented relationship upon a flexible body 32.

The flexible body 32 is made of a polymeric, electrically nonconductive material, like polyethylene or polyurethane. The body 32 carries within it the resilient bendable wire or spring with attached steering wires (best shown in FIGS. 20 and 23), so it can be flexed to assume various curvilinear shapes.

The segmented electrodes 30 comprise solid rings of conductive material, like platinum. The electrode rings 30 are pressure fitted about the body 32. The flexible portions of the body 32 between the rings 30 comprise electrically nonconductive regions.

The body 32 can be flexed between the spaced apart electrodes 30 to bring the electrode 30 into intimate contact along a curvilinear surface of the heart wall, whether the heart surface curves outward (as FIG. 3 shows) or curves inward (as FIG. 4 shows).

FIG. 5 shows an implementation of another preferred type of a flexible ablating element, of the same general style as element 10(1), designated 10(2). Element 10(2) includes two generally rigid electrode elements 34 and 36 arranged in a spaced apart relationship at the distal tip of a flexible body 38. The flexible body 38 is made of electrically insulating material, like polyurethane and PEBAX® plastic material. The body 38 carries one relatively large, rigid metal electrode 34 at its tip, which comprises a body of electrically conductive material, like platinum. The body 38 also carries another rigid electrode 36, which comprises a solid ring 36 of electrically conductive material, like platinum, pressure fitted about the. body 38. As FIG. 5 shows, the ablating element 10(2) can also include one or more conventional sensing ring electrodes 40 proximally spaced from the ablating ring electrode 36. The sensing ring electrodes 40 serve to sense electrical events in heart tissue to aid the physician in locating the appropriate ablation site.

As shown in phantom lines in FIG. 5, the flexible body 38, when pressed against the endocardial surface targeted for ablation, bends to place the sides of the rigid electrodes 34 and 36 in intimate contact against the particular contour of the surface. The flexible nature of the ablating element 10(2) can be further augmented by the inclusion of the resilient bendable wire or spring 26 within it (best shown in FIG. 27). In this embodiment, the steering wires 24 connect to the left and right sides of the bendable wire 26. The opposite ends of the steering wires 24 connect to a steering mechanism of the type previously described and shown in FIG. 2. In this arrangement, the physician can use the steering mechanism to remotely flex the electrodes 34 and 36 in the manner shown in FIG. 5.

Figure 27:
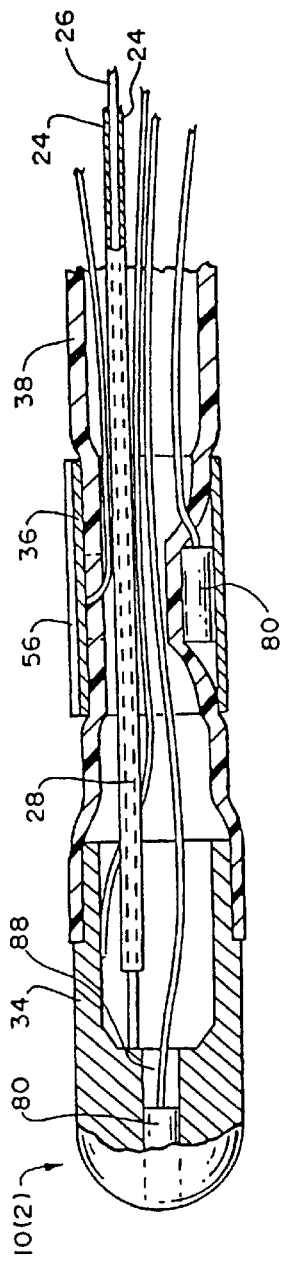
FIGS. 27 and 28 are side section views of the mounting of temperature sensing elements on the ablating element shown in FIG. 5.

Preferably, as FIG. 27 shows, the steering wires 24 are secured to the bendable wire 26 near its distal end, where the bendable wire 26 is itself secured to the tip electrode 34. Bending of the wire 26 thereby directly translates into significant relative flexing of the distal end of the catheter body 38, which carries the electrodes 34 and 36.

Alternatively, the region between the electrodes 34 and 36 can be stiff, not flexible. In this arrangement, pressing the 34 and 36 against tissue brings the tissue into conformance about the electrodes 34 and 36.

The generally rigid, segmented electrodes 30 in element 10(1) and 34/36 in element 10(2) can be operated, at the physician's choice, either in a unipolar ablation mode or in a bipolar mode. In the unipolar mode, ablating energy is emitted between one or more the electrodes 30 (in element 10(1)) or electrodes 34/36 (in element 10(2)) and an external indifferent electrode. In the bipolar mode, ablating energy is emitted between two of the electrodes 30 (in element 10(1)) or the electrodes 34 and 36 (in element 10(2)), requiring no external indifferent electrode.

B. Flexible Electrode Elements

FIG. 6 shows an implementation of another preferred style of a flexible ablating element, designated 10(3). The element 10(3), unlike elements 10(1) and 10(2), includes generally flexible electrode elements 44 carried on a likewise flexible body 42.

The flexible body 42 is made of a polymeric, electrically nonconductive material, like polyethylene or polyurethane, as the flexible body of elements 10(1) and 10(2). The body 42 also preferably carries within it the resilient bendable wire or spring 26 with attached steering wires 24 (best shown in FIGS. 29 and 30), so it can be flexed to assumed various curvilinear shapes, as FIG. 6 shows.

The body 32 carries on its exterior surface an array of segmented, generally flexible electrodes 44 comprising spaced apart lengths of closely wound, spiral coils. The coil electrodes 44 are made of electrically conducting material, like copper alloy, platinum, or stainless steel. The electrically conducting material of the coil electrode 44 can be further coated with platinum-iridium or gold to improve its conduction properties and biocompatibility.

Figure 7A:
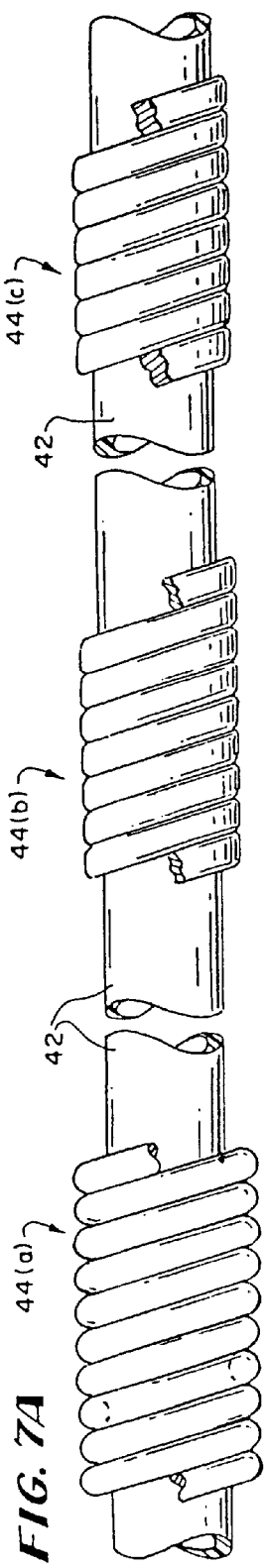
FIGS. 7A/B are, respectively, side and side section views of different wrapped wire coils comprising flexible electrode elements.
Figure 7B:
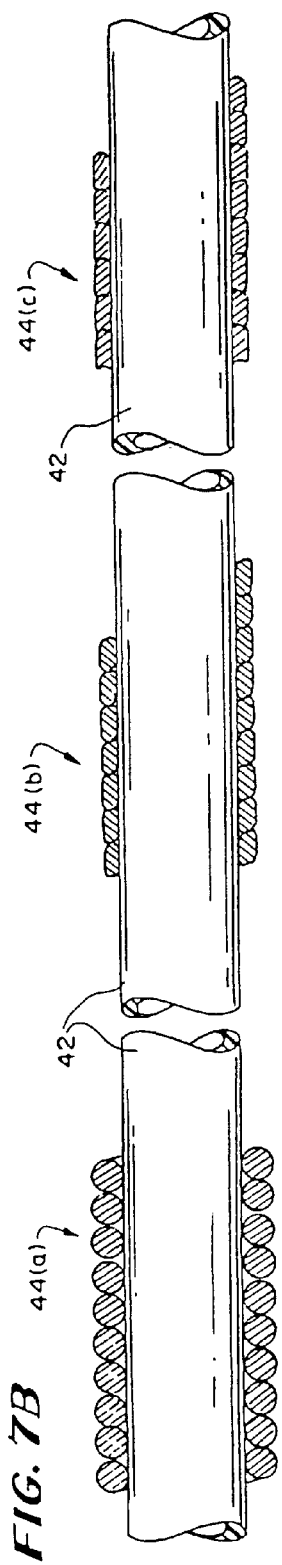

The coils 44 can be made of generally cylindrical wire, as the coil 44(a) shown in FIGS. 7A/B. Alternatively, the wire forming the coils 44 can be non-circular in cross section. The wire, for example, have a polygon or rectangular shape, as the coil 44(b) shown in FIGS. 7A/B. The wire can also have a configuration in which adjacent turns of the coil nest together, as the coil 44(c) shown in FIGS. 7A/B. Coils 44(b) and 44(c) in FIGS. 7A/B present a virtually planar tissue-contacting surface, which emulates the tissue surface contact of the generally rigid electrode 30 shown in FIGS. 3 and 4. However, unlike the electrode 30, the coils 44(b) and 44(c), as well as the cylindrical coil 44(a), are each inherently flexible and thereby better able to conform to the surface contour of the tissue.

Figure 8B:
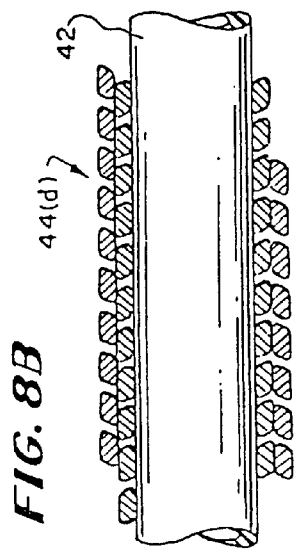
FIGS. 8A/B are, respectively, a side and side section view of multiple wrapped wire coils comprising a flexible electrode element.
Figure 8A:

In another alternative arrangement, each coil 44 can comprise multiple, counter wound layers of wire, as the coil 44(d) shown in FIGS. 8A/B. This enhances the energy emitting capacity of the coil 44(d), without significantly detracting from its inherent flexible nature. The multiple layer coil 44(d) structure can also be formed by using a braided wire material (not shown).

An alternative arrangement (shown in FIG. 9) uses the generally rigid tip electrode 34 (like that in element 10(2), shown in FIG. 5) in combination with a generally flexible electrode segment 44 made of a closely wound coil. Of course, the tip electrode 34, too, could comprise a generally flexible electrode structure made of a closely wound coil. It should be apparent by now that many combinations of rigid and flexible electrode structures can be used in creating a flexible ablating element.

Figure 10:
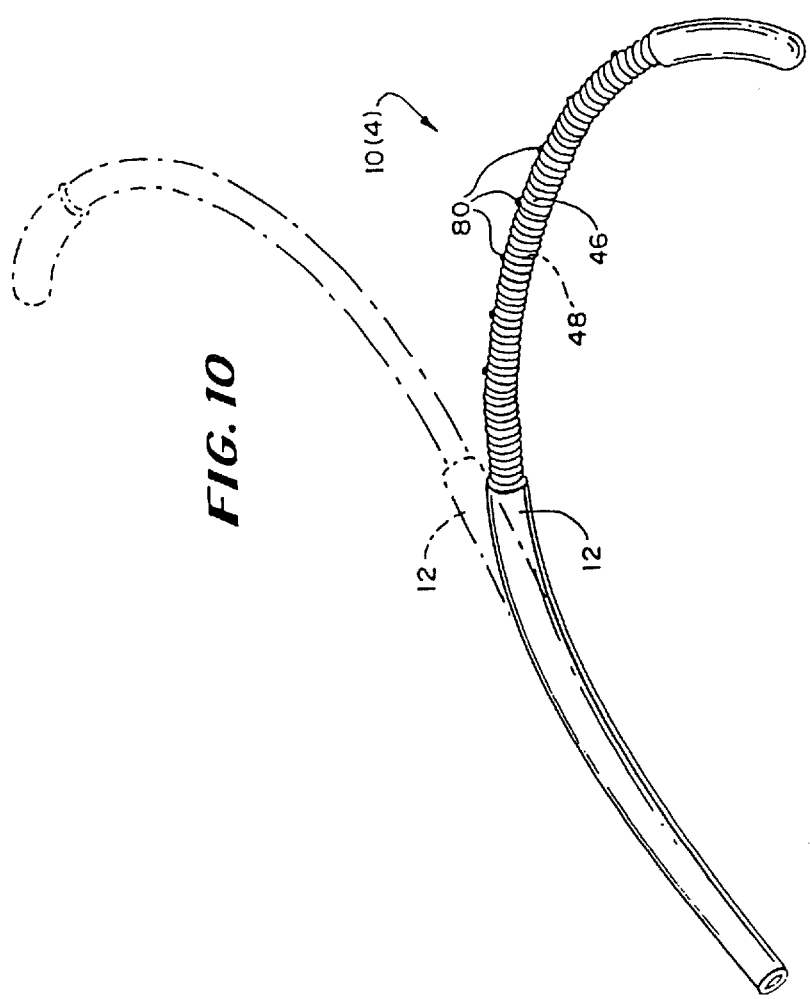
FIG. 10 is a perspective view of a continuous flexible electrode element comprising a wrapped wire coil.

Furthermore, the inherent flexible nature of a coiled electrode structures 44 makes possible the construction of a flexible ablating element (designated 10(4) in FIG. 10) comprising a continuous elongated flexible electrode 46 carried by a flexible body 48. The continuous flexible electrode 46 comprises an elongated, closely wound, spiral coil of electrically conducting material, like copper alloy, platinum, or stainless steel, wrapped about the flexible body. For better adherence, an undercoating of nickel or titanium can be applied to the underlying flexible body. The continuous coil electrode 46 can be arranged and configured in the same fashion as the segmented coil electrodes 44 shown in FIGS. 7A/B and 8A/B.

The continuous coil electrode 46 is flexible and flexes with the underlying body 48, as FIG. 10 shows. It can be easily placed and maintained in intimate contact against heart tissue. The continuous flexible coil structure shown in FIG. 10 therefore makes possible a longer, flexible ablating element.

In an alternative arrangement (shown in FIGS. 12A/B), the elongated coil electrode 46 can include a sliding sheath 50 made of an electrically nonconducting material, like polyimide. A stylet (not shown) attached to the sheath 50 extends through the associated catheter body 12 to a sliding control lever carried on the probe handle 16 (also not shown). Moving the sheath 50 varies the impedance of the coil electrode 46. It also changes the surface area of the element 10(4).

Further details of this embodiment can be found in copending U.S. patent application Ser. No. 08/137,576, filed Oct. 15, 1993, and entitled "Helically Wound Radio Frequency Emitting Electrodes for Creating Lesions in Body Tissue," which is incorporated into this Specification by reference.

Figure 11:
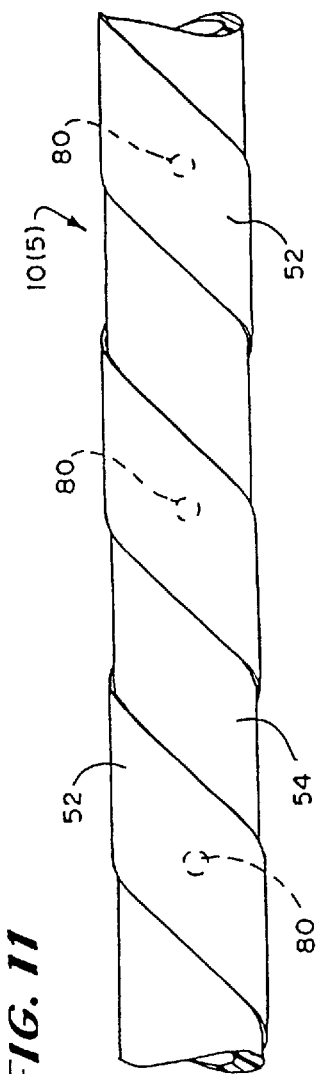
FIG. 11 is a perspective view of a continuous flexible electrode element comprising a wrapped ribbon.

FIG. 11 shows another implementation of a generally flexible element, designated element 10(5). The element 10(5) comprises a ribbon 52 of electrically conductive material wrapped about a flexible body 54. The ribbon 52 forms a continuous, inherently flexible electrode element.

Alternatively, the flexible electrodes can be applied on the flexible body by coating the body with a conductive material, like platinum-iridium or gold, using conventional coating techniques or an ion beam assisted deposition (IBAD) process. For better adherence, an undercoating of nickel or titanium can be applied. The electrode coating can be applied either as discrete, closely spaced segments (to create an element like 10(3)) or in a single elongated section (to create an element like 10(4) or 10(5)).

The flexible electrodes of elements 10(3) can be operated, at the physician's choice, either in a unipolar ablation mode or in a bipolar mode.

C. Controlling Lesion Characteristics Using Flexible Electrodes

The ablating elements 10(1) to 10(5), as described above, are infinitely versatile in meeting diverse tissue ablation criteria.

For example, the ablating elements 10(1) and 10(3) to 10(5) can be conditioned to form different configurations of elongated (i.e., generally long and thin) lesion patterns. These elongated lesion patterns can be continuous and extend along a straight line (as lesion pattern 200 in FIG.

33A shows) or along a curve (as lesion pattern 204 in FIG. 34A shows). Alternatively, these elongated lesion patterns can be segmented, or interrupted, and extend along a straight line (as lesion pattern 202 in FIG. 33B shows) or along a curve (as lesion pattern 206 in FIG. 34B shows). Elongated lesion patterns can be used to treat, for example, atrial fibrillation.

Alternatively, the ablating elements 10(1) to 10(5) can be conditioned to form larger and deeper lesions in the heart, as lesion pattern 208 in FIG. 35 shows. These lesion large and deep lesion patterns can be used to treat, for example, atrial flutter or ventricular tachycardia.

The characteristics of lesions formed by the ablating elements 10(1) to 10(5) can be controlled in various ways. For example, lesion characteristics are controlled by employing one or more of the following techniques:

(i) selectively adjusting the size and spacing of energy emitting regions along the elements.

(ii) selectively masking the energy emitting regions on the elements to focus ablating energy upon the targeting tissue.

(iii) selectively altering the electrical connections of wires conveying ablating energy to the energy emitting regions on the elements, to thereby affect the distribution of ablation energy.

(iv) selectively altering the shape of the flexible support body, to thereby affect the distribution and density of energy emitting regions on the elements.

(v) selectively controlling temperature conditions along the energy emitting regions of the elements.

These various techniques of controlling lesion characteristics will now be individually discussed in greater detail.

1. Size and Spacing of Energy Emitting Regions

The number of electrode segments that the elements 10(1), (2); (4); and (5) carry, and the spacing between them, can vary, according to the particular objectives of the ablating procedure. Likewise, the dimensions of individual electrode segments and underlying body in elements 10(1) to 10(5) can also vary for the same reason. These structural features influence the characteristics of the lesion patterns formed.

The continuous electrode structure of 10(4) is well suited for creating continuous, elongated lesion patterns like the patterns 200 and 204 shown in FIGS. 33A and 34A, when the entire electrode is conditioned to emit energy. The segmented electrode structures of elements 10(1); (3); and (5) are also well suited for creating continuous, elongated lesion patterns like the pattern 200 shown in FIG. 33A, provided that the electrode segments are adjacently spaced close enough together to create additive heating effects when ablating energy is transmitted simultaneously to the adjacent electrode segments. The same holds true when the continuous electrode structure 10(4) is conditioned to function like a segmented electrode structure by emitting energy from adjacent zones along its length, in which case the zones serve as electrode segments. Stated another way, the segments comprise zones which emit energy to tissue to obtain the desired therapeutic tissue heating effect.

The additive heating effects along a continuous electrode structure or between close, adjacent electrode segments intensify the desired therapeutic heating of tissue contacted by the segments. The additive effects heat the tissue at and between the adjacent electrode segments to higher temperatures than the electrode segments would otherwise heat the tissue, if conditioned to individually emit energy to the tissue, or if spaced apart enough to prevent additive heating effects. The additive heating effects occur when the electrode segments are operated simultaneously in a bipolar mode between electrode segments. Furthermore, the additive heating effects also arise when the continuous electrode or electrode segments are operated simultaneously in a unipolar mode, transmitting energy to an indifferent electrode.

Conversely, when the energy emitting segments are not sufficiently spaced close enough to each other to generate additive heating effects, the continuous electrode structure 10(4) and the segmented electrode structures 10(1); (3); and (5) create elongated, segmented lesion patterns like the pattern 202 shown in FIG. 33B.

More particularly, when the spacing between the segments is equal to or less than about 3 times the smaller of the diameters of the segments, the simultaneous emission of energy by the segments, either bipolar between the segments or unipolar to an indifferent electrode, creates. an elongated continuous lesion pattern in the contacted tissue area due to the additive heating effects. Conversely, when the spacing between the segments is greater than about 5 times the smaller of the diameters of the segments, the simultaneous emission of energy by the segments, either bipolar between segments or unipolar to an indifferent electrode, does not generate additive heating effects. Instead, the simultaneous emission of energy by the zones creates an elongated segmented, or interrupted, lesion pattern in the contacted tissue area.

Alternatively, when the spacing between the segments along the contacted tissue area is equal to or less than about 2 times the longest of the lengths of the segments the simultaneous application of energy by the segments, either bipolar between segments or unipolar to an indifferent electrode, also creates an elongated continuous lesion pattern in the contacted tissue area due to additive heating effects. Conversely, when the spacing between the segments along the contacted tissue area is greater than about 3 times the longest of the lengths of the segments, the simultaneous application of energy, either bipolar between segments or unipolar to an indifferent electrode, creates an elongated segmented, or interrupted, lesion pattern.

The continuous electrode structure 10(4) and the segmented electrode structures 10(1); (3); and (5), when flexed can also create curvilinear lesion patterns like the patterns 204 and 206 shown in FIGS. 34A and 34B. The peripheral shape of the lesion pattern can be controlled by flexing the body from straight to curvilinear. As already explained, the body can be remotely steered to flex it into a desired shape, or it can possess a preformed shape memory. In the latter situation, removing a constraint (such as a sheath, not shown), enables the operator to change the segment from straight to curvilinear.

To consistently form these curvilinear lesion patterns, additional spacial relationships among the electrode segments must be observed. The particular nature of these relationships depends in large part upon the length to diameter ratio of the individual electrode segments.

More particularly, when the length of each energy applying segment is equal to or less than about 5 times the diameter of the respective segment, the curvilinear path that support element takes should create a distance across the contacted tissue area that is greater than about 8 times the smaller of the diameters of the first and second zones. In this arrangement, the simultaneously application of energy forms an elongated lesion pattern in the tissue area that follows the curved periphery contacted by the support element, but does not span across the contacted tissue area.

The curvilinear lesion pattern is continuous (as FIG. 34A shows) if the spacing between the segments along the support element is sufficient to create an additive heating effect between the segments, as above described. Otherwise, the curvilinear lesion pattern is segmented or interrupted along its length, as FIG. 34B shows.

When the length of each energy applying segment is greater than about 5 times the diameter of the respective segment (which generally results in an elongated electrode structure like 10(4)), the curvilinear path that support element takes should create a radius of curvature that is greater than about 4 times the smallest the diameters segments. In this arrangement, the simultaneous application of energy by the segments (by the entire elongated electrode) forms an elongated lesion pattern in the tissue area that follows the curved periphery contacted by the support element, but does not span across the contacted tissue area. Again, the curvilinear lesion pattern is continuous if the spacing between the energy applying segments along the support body is sufficient to create an additive heating effect. Otherwise, the curvilinear lesion pattern is segmented or interrupted along its length.

Wider and deeper. lesion patterns uniformly result by increasing the surface area of the individual segments, due to the extra additive effects of tissue heating that the larger segments create. For this reason, the larger surface areas of the electrode segments 34/36 in element 10(2) are most advantageously used for forming large and deep lesion patterns, provided that both electrode segments 34/36 are conditioned to emit ablating energy simultaneously.

However, with all elements 10(1) to 10(5), ablating energy can be selectively applied individually to just one or a selected group of electrode segments, when desired, to further vary the size and characteristics of the lesion pattern.

Taking the above considerations into account, it has been found that adjacent electrode segments having lengths of less than about 2 mm do not consistently form the desired continuous lesion patterns. Using rigid electrode segments, the length of the each electrode segment can vary from about 2 mm to about 10 mm. Using multiple rigid electrode segments longer than about 10 mm each adversely effects the overall flexibility of the element 10(1).

However, when flexible electrode segments are used, electrode segments longer that about 10 mm in length can be used. Flexible electrode segments can be as long as 50 mm. If desired, the flexible electrode structure can extend uninterrupted along the entire length of the body, thereby forming the continuous elongated electrode structure 46 of element 10(4).

In the electrode structures of elements 10(1) to 10(5), the diameter of the electrode segments and underlying flexible body can vary from about 4 french to about 10 french. When flexible electrode segments are used (as in elements 10(3) to 10(5)), the diameter of the body and electrode segments can be less than when more rigid electrode segments are used (as in element 10(1)). Using rigid electrodes, the minimum diameter is about 1.35 mm, whereas flexible electrodes can be made as small as about 1.0 mm in diameter.

In a representative segmented electrode structure using rigid electrode segments, the flexible body is about 1.35 mm in diameter. The body carries electrode segments each having a length of 3 mm. When eight electrode segments are present and simultaneously activated with 100 watts of radio frequency energy for about 60 seconds, the lesion pattern is long and thin, measuring about 5 cm in length and about 5 mm in width. The depth of the lesion pattern is about 3 mm, which is more than adequate to create the required transmural lesion (the atrial wall thickness is generally less than 3 mm).

In a representative segmented electrode structure using flexible electrode segments, the coil electrode 56 is about 1.3 mm in diameter, but could be made as small as 1.0 mm in diameter and as large as 3.3 mm in diameter. In this arrangement, the coil electrode 56 is about 5 cm in total length. When activated with 80 watts of radio frequency energy for 60 seconds, the coil electrode 56 forms a contiguous lesion pattern that is about 3 mm in width, about 5 cm in length, and about 1.5 mm in depth.

Figure 9:
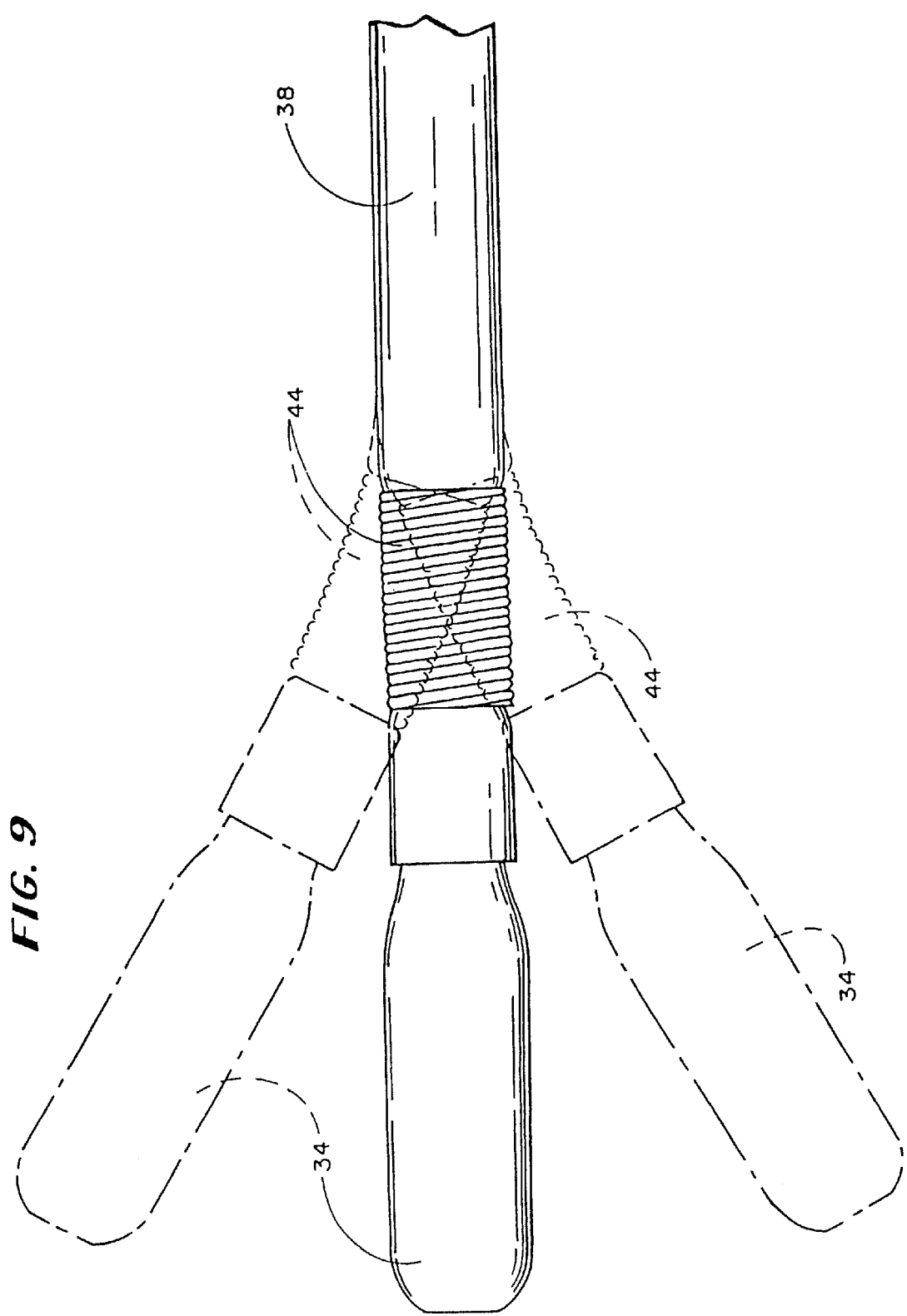
FIG. 9 is a side view of a flexible ablating element comprising a rigid tip electrode element and a flexible body electrode segment.

Regarding the ablating element 10(2), the tip electrode 34 can range in length from about 4 mm to about 10 mm. The electrode segment 36 can vary in length from about 2 mm to about 10 mm (or more, if it is a flexible elongated electrode, as FIG. 9 shows). The diameter of the electrodes 34 and 36, and thus the flexible body 38 itself, can vary from about 4 french to about 10 french.

In element 10(2), the distance between the two electrodes 34 and 36 can also vary, depending upon the degree of flexibility and the size of the lesion pattern required. In a representative embodiment, the electrode segment 36 is spaced from the tip electrode 34 by about 2.5 mm to about 5 mm. Thus, the effective ablating length presented by the combined electrodes 34 and 36 can vary from about 8.5 mm to about 25 mm. Preferably, the effective ablating length presented is about 12 mm.

2. Focusing Ablating Energy

As shown in FIGS. 13A/B, a side of one or more electrode segments of elements 10(1), (2), and (3) (generally designated $E_{SEG}$ in FIG. 13A), or a side of at least a portion of the continuous elongated electrode of element 10(4), and 10(5) (generally designated $E_{COW}$ in FIG. 13B), can be covered with a coating 56 of an electrically and thermally insulating material. This coating 56 can be applied, for example, by brushing on a UV-type adhesive or by dipping in polytetrafluoroethylene (PTFE) material.

The coating 56 masks the side of the electrode $E_{SEG}$ and $E_{COW}$ that, in use, is exposed to the blood pool. The coating 56 thereby prevents the transmission of ablating energy directly into the blood pool. Instead, the coating 56 directs the applied ablating energy directly toward and into the tissue.

The focused application of ablating energy that the coating 56 provides helps to control the characteristics of the lesion. The coating 56 also minimizes the convective cooling effects of the blood pool upon the electrode $E_{SEG}$ and $E_{COW}$ while ablating energy is being applied, thereby further enhancing the efficiency of the lesion formation process.

3. Uniformly Distributing Ablating Energy

As FIG. 14A shows, the segmented electrodes $E_{SEG}$ are electrically coupled to individual wires 58, one serving each electrode segment, to conduct ablating energy to them. As FIG. 15A shows, in the case of a segmented coil electrode, the end of the connecting wire 50 itself can be wrapped about the flexible body to form a flexible coil segment 44.

In the case of a continuous elongated electrode structure (like coil electrode 46 of element 10(4)), wires 58 are preferable electrically coupled to the coil 46 at equally spaced intervals along its length. This reduces the impedance of the coil along its length. As already explained, and as FIGS. 12A/B show, the elongated coil electrode can also include a sliding sheath 50 to vary the impedance.

In an alternative embodiment, shown in FIG. 14B, there are two spaced apart wires 58(1) and 58(2) electrically coupled to each segmented electrode $E_{SEG}$. In this arrangement, power is delivered in parallel to each segmented electrode $E_{SEG}$. This decreases the effect of voltage gradients within each segmented electrode $E_{SEG}$, which, in turn, improves the uniformity of current density delivered by the electrode $E_{SEG}$. The spacing between the multiple wires serving each electrode segment $E_{SEG}$ can be selected to achieve the uniformity of current density desired.

Figure 15B:
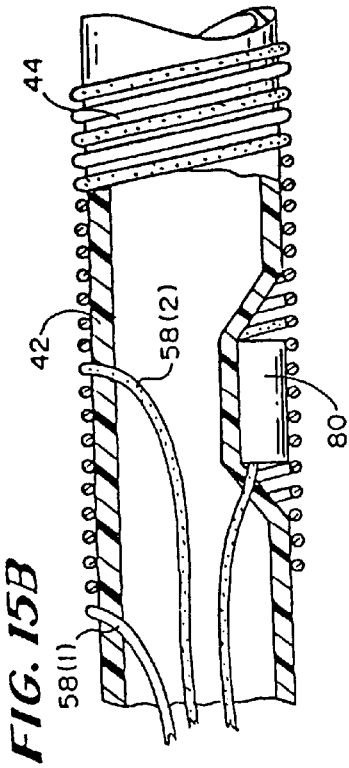
FIGS. 15A/B are side section views of forming flexible coil segments from the electrical conducting wires.
Figure 15A:
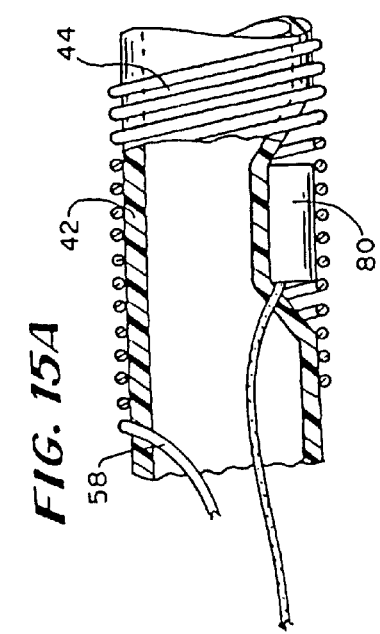

As FIG. 15B shows, each flexible coil segment 44 can also comprise two or more individual wires 58(1) and 58(2) wrapped at their ends, which together form the coil segment. The multiple wires can be wrapped sequentially or in a staggered arrangement to form the coil segment. Similarly, an elongated flexible electrode can be formed by individual lengths of wire wrapped about the body, either sequentially or in a staggered pattern.

4. Distribution and Density of Energy Applying Segments

Figure 16B:
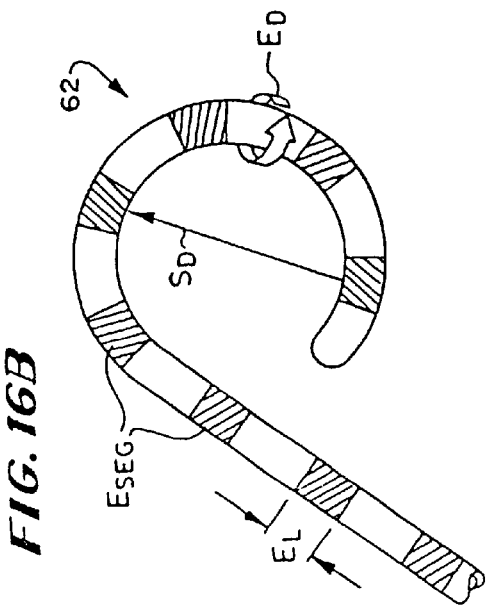
FIGS. 16A/B are views of various shaped multiple electrode structures for making lesions that span across diagonally and/or diametric spaced electrode regions.
Figure 16A:
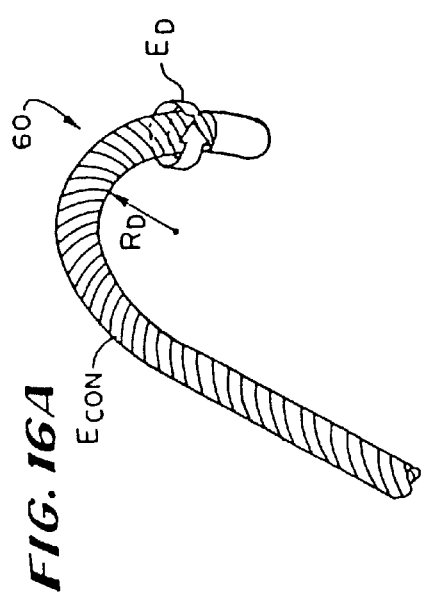

The flexible ablating elements 10(1) and 10(3) to 10(5) can also be used to form larger and deeper lesion patterns by specially shaping the support body to increase the density of electrodes per given tissue area. Structures suited for creating larger lesion patterns result when the flexible body is generally bent back upon itself to position electrode regions either diagonally close to each other (as structure 60 in FIG. 16A shows) or both diagonally close and diametrically facing each other (as structure 62 in FIG. 16B shows). The electrode regions can be either energy emitting portions of a continuous flexible electrode $E_{COW}$ as in structure 60 in FIG. 16A, or energy emitting segments $E_{SEG}$ of a segmented electrode structure, as in structure 62 in FIG. 16B.

This close diagonal spacing and/or close diametric facing of electrodes that the structures 60 and 62 provide, coupled with the simultaneous emission of ablating energy by the electrodes on the structures 60 and 62, significantly concentrates the distribution of ablating energy. These specially shaped electrode structures 60 and 62 provide an additive heating effect that causes lesions to span across electrodes that are diagonally close and/or diametrically facing. The spanning lesions create large and deep lesion patterns in the tissue region that the structures 60 and 62 contact.

The structures 60 and 62 best provide these larger and deeper lesion patterns when they maintain a prescribed relationship among the electrode regions that takes into account the geometry of the structure, the dimension of the structure, and the dimension of the electrode regions it carries.

More particularly, when the length of each energy emitting region or zone is greater than about 5 times the diameter of the respective region or zone (as would be the case in the continuous electrode $E_{COW}$ in FIG. 16A, or with a segmented electrode having large electrode segments), the support structure should be bent back upon itself to maintain a minimum radius of curvature (designated $R_D$ in FIG. 16A) that does not exceed about 3.5 times the diameter of the smallest electrode area (designated $E_D$ in FIG. 16A). The support structure can be shaped as a hook (as structure 60 in FIG. 16A) or as a circle (as structure 62 in FIG. 16B) to present this minimum radius of curvature.

When the support structure establishes and maintains this relationship, the emission of ablating energy by the electrode $E_{COW}$ along its length will create a lesion that spans across the interior of the structure 60 or 62, between the diagonal and facing electrode regions, due to additive heating effects. A large and deep lesion pattern like the pattern 208 shown in FIG. 35 results, which occupies essentially all of the interior region enclosed by the structure 60 or 62. For uniformity of lesion generation, $R_D$ should preferably not exceed about 2.5 times $E_D$. Most preferably, $R_D$ is less than about 1.5 times $E_D$.

Conversely, as described earlier, with energy emitting segments of this size, if the curvilinear path that support element takes creates a radius of curvature $R_D$ that is greater than about 4 times the smallest the diameters segments, the simultaneous emission of energy by the segments forms an elongated lesion pattern in the tissue area that follows the curved periphery contacted by the support element, but does not span across the contacted tissue area (like the lesion patterns 204 and 206 shown in FIGS. 34A and 34B). The curvilinear lesion pattern is continuous, as shown in FIG. 34A, if the spacing between the energy emitting segments along the support body is sufficient close to create an additive heating effect between the segments, as would be the case for a continuous electrode or closely spaced large segmented electrodes. Otherwise, the curvilinear lesion pattern is segmented or interrupted along its length, as in FIG. 34B.

When the length of each energy applying region or zone is less than or equal to about 5 times the diameter of the respective region or zone (as would be the case of an array of smaller segmented electrodes $E_{SEG}$ like elements 10(1) and 10(3) and as shown in FIG. 16B), the support structure should be bent back upon itself so that the longest distance between facing electrode pairs diagonally or diametrically spaced to provide an additive heat effect (designated $S_D$ in FIG. 16B) does not exceed about 7 times the diameter of the smallest electrode segment (also designated $E_D$ in FIG. 16B). In isoradial. circular or hook shaped configurations, the longest distance $S_D$ will occur between diametrically facing electrode segments (as FIG. 16B shows). When facing electrode segments, subject to the above constraints, emit ablating energy simultaneously, a lesion uniformly spanning the space between them will result due to additive heating effects. A large deep lesion uniformly occupying the region enclosed by the structure will be formed, as FIG.. 35 shows.

For uniformity of lesion generation, $S_D$ should be also preferably no greater than about 5 times, and most preferably no greater than 3 times, $E_D$. Conversely, if $S_D$ exceeds about 8 times $E_D$, a long and thin lesion pattern results, which follows the periphery of the structure, but does not uniformly span across the interior of the structure 60 between diagonal or facing electrode regions. The curvilinear lesion pattern is continuous, as shown. in FIG. 34A, if the spacing between the energy applying segments along the support body is sufficient close to create an additive heating effect between the segments, as would be the case for a continuous electrode or closely spaced large segmented electrodes. Otherwise, the curvilinear lesion pattern is segmented or interrupted along its length, as in FIG. 34B.

Preferably, to further assure uniformity of lesion generation when segmented electrodes are used, the $S_D$ of the support structure 62 should not exceed about 4 times the length of the longest facing segment (designated $E_L$ in FIG. 16B). Most preferably, in a segmented electrode structure for creating large deep lesions, $S_D$ should be less than about 3 times $E_L$. This criterion holds true when the length is not substantially larger than the diameter. When the length is more than about 5-fold larger than the diameter, the ablating element is similar to a continuous electrode and the determining criterion for the lesion structure is the diameter of the ablation structure.

A large lesion can be created by placing in parallel facing relationship 6 mm apart, two energy applying segments that are each 8F in diameter and 3 mm in length, and applying RF energy simultaneously to both segments. When the application of energy by both segments is controlled to maintain temperatures at the segments of 80° C. for two minutes, the lesion width is about 12 mm, the lesion length is about 4 mm, and the lesion depth is about 7 mm.

Structures like those shown in FIGS. 16A and B that meet the above criteria can be variously constructed, depending upon the particular ablation objectives desired. They can be in the shape of a doubled back, open circular structure like a hook (as structure 60 generally represents), or a closed or concentric spiral structure (as structure 62 generally represents).

Figure 17B:
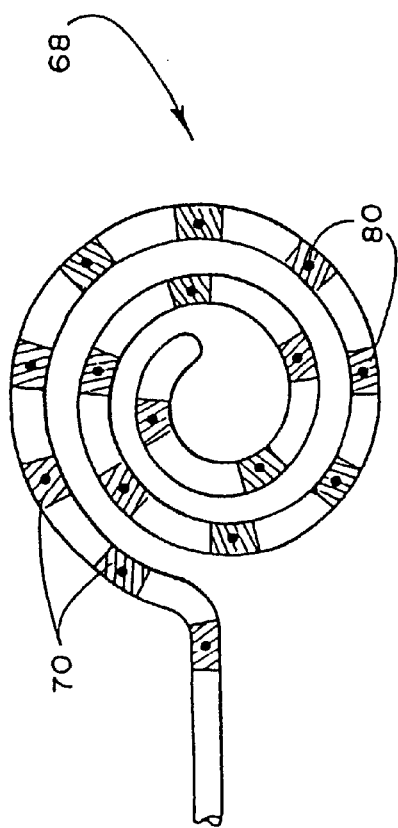
FIGS. 17B/18B are views of a generally spiral multiple electrode structure for making lesions that span across diagonally and/or diametric spaced electrode regions.
Figure 18B:
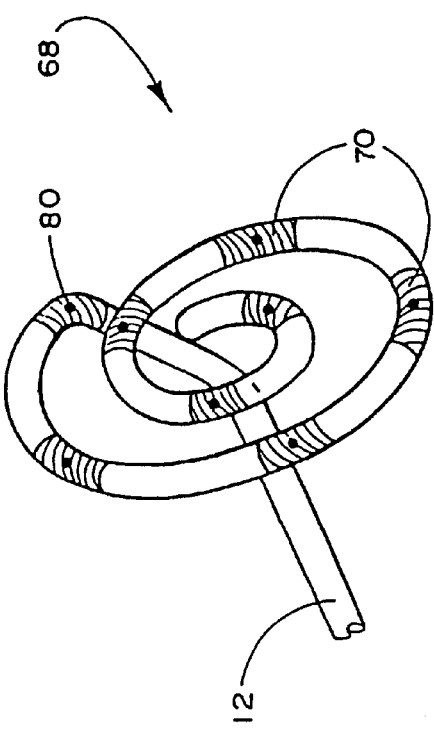
Figure 17A:
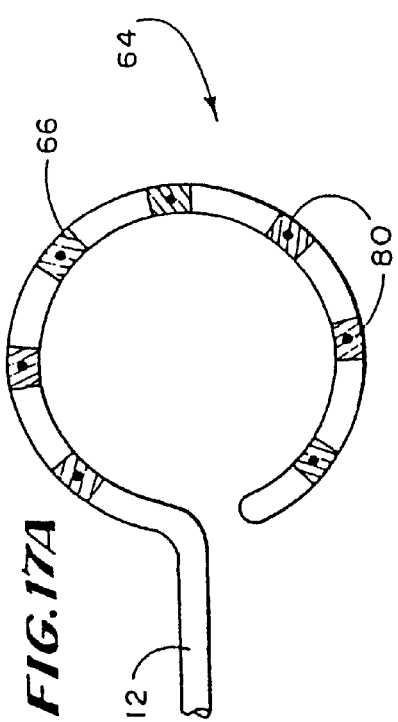
FIGS. 17A/18A are views of a generally circular multiple electrode structure for making lesions that span across diagonally and/or diametric spaced electrode regions.
Figure 18A:
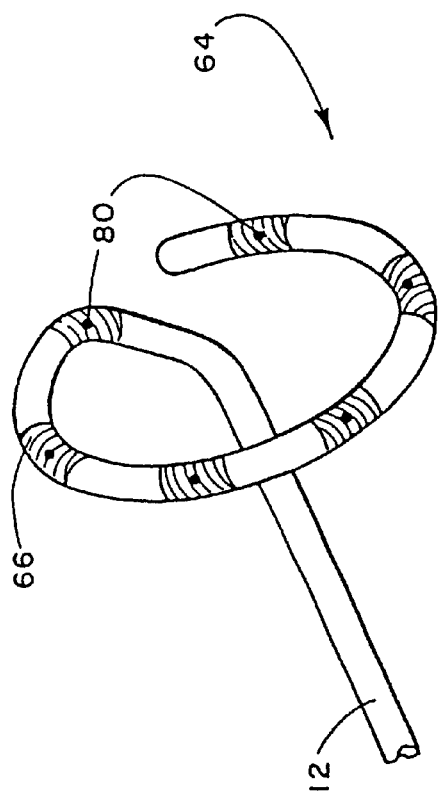

As a further example, a preshaped circular structure 64 like FIGS. 17A and 18A show can be used for creating lesion patterns for treating atrial fibrillation. The structure 64 can extend axially from the distal end of the catheter body 12, as FIG. 17A shows. Alternatively, the structure 64 can extend generally perpendicular to the distal end of the catheter body, as FIG. 18A shows. The structure 64 can either carry rigid or flexible electrode segments 66 (as FIGS. 17A and 18A show), or, alternatively, the structure 64 can carry a continuous flexible electrode along its length.

As another example, a preshaped spiral structure 68 like FIGS. 17B and 18B show can be used to form large lesion patterns for treating ventricular tachycardia. The structure 68 can extend axially from the distal end of the catheter body 12, as FIG. 17B shows. Alternatively, the structure 68 can extend generally perpendicular to the distal end of the catheter body, as FIG. 18B shows. The structure 68 can either carry flexible electrode segments 70 (as FIG. 17B and 18B show), or, alternatively, the structure 64 can carry a continuous flexible electrode along its length. The longest distance between the facing electrodes throughout the spiral determines whether the lesion will span the regions between electrodes when they are simultaneously supplied with energy, following the criterion established above. If the above criterion is met, then the resulting lesion will be large and deep.

Further details of the spiral structure 68 are described in copending patent application Ser. No. 08/138,452, filed Oct. 14, 1993, and entitled "Systems and Methods for Locating and Ablating Accessory Pathways in the Heart," which is incorporated herein by reference.

As yet another example, a preshaped hoop structure 72 like FIGS. 19A/B/C show can be used to create lesion patterns useful in treating atrial fibrillation. The hoop structure 72 extends generally perpendicular from the distal end of the catheter body 12. As shown in FIG. 19A, the hoop structure 72 can carry a continuous flexible electrode 74. Alternatively, the structure 72 can carry segmented flexible electrodes 76, as FIG. 19B shows. Still alternatively, the structure 72 can carry rigid electrode segments 78.

5. Temperature Control at Multiple Energy Emitting Regions

In the illustrated and preferred embodiments, each flexible ablating element 10(1) to 10(5) carries at least one and, preferably, at least two, temperature. sensing element 80. The multiple temperature sensing elements 80 measure temperatures along the length of the element 10.

(i) Temperature Sensing with Rigid Electrode Elements

In the segmented element 10(1) (see FIGS. 3 and 4), each electrode segment 30 preferably carries at least one temperature sensing element 80. In this configuration, the sensing elements 80 are preferably located in an aligned relationship along one side of each segmented electrode 30, as FIGS. 3 and 4 show.

The body 32 preferably carries a fluoroscopic marker (like the stripe 82 shown in FIGS. 3 and 4) for orientation purposes. The stripe 82 can be made of a material, like tungsten or barium sulfate, which is extruded into the tubing 12. The extruded stripe can be fully enclosed by the tubing or it can be extruded on the outer diameter of the tubing making it visible to the eye. FIG. 5 shows the marker in the wall of the tubing 12. An alternative embodiment can be a fluoro-opaque wire like platinum or gold which can be extruded into the tubing wall. Yet another embodiment is to affix a marker in the inner diameter of the tubing during manufacturing.

The sensing elements 80 can be on the same side as the fluoroscopic marker 82 (as FIGS. 3 and 4 show), or on the opposite side, as long as the physician is aware of the relative position of them. Aided by the marker 82, the physician orients the element 10(1) so that the temperature sensing elements 80 contact the targeted tissue.

Alternatively, or in combination with the fluoroscopic marker 82, the sensing elements 80 can be consistently located on the inside or outside surface of element 10(1) when flexed in a given direction, up or down. For example, as FIG. 3 shows, when the element 10(1) is flexed to the down, the sensing elements 80 are exposed on the inside surface of the element 10(1). As FIG. 4 shows, when the element 10(1) flexed to the upward, the sensing elements 80 are exposed on the outside surface of the element 10(1).

Figure 20:
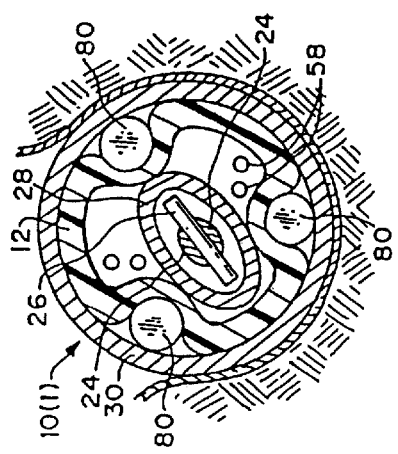
FIG. 20 is an end section view of an ablating electrode element carrying one temperature sensing element.
Figure 21:
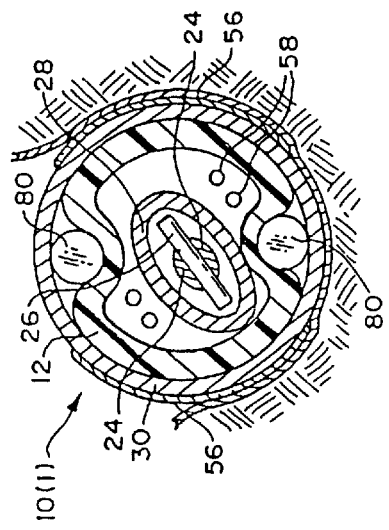
FIG. 21 is an end section view of an ablating electrode element carrying two temperature sensing elements.
Figure 22:
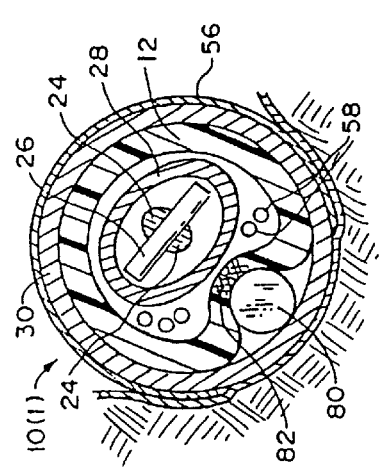
FIG. 22 is an end section view of an ablating electrode element carrying three temperature sensing elements.

Each electrode segment 30 can carry more than a single temperature sensing element 80. As FIGS. 20 to 22 show, each electrode segment 30 can carry one, two, three, or more circumferentially spaced apart temperature sensing elements 80. The presence of multiple temperature sensing elements 80 on a single electrode segment 30 gives the physician greater latitude in positioning the ablating element 10(1), while still providing temperature monitoring.

As FIG. 20 shows, a mask. coating 56, as above described, can also be applied to the side of the single sensor-segmented electrode 30 opposite to the temperature sensing element 80, which, in use, is exposed to the blood pool. As FIG. 21 shows, the mask coating 56 lies between the two sensors 80 on the bi-directional segmented electrode 30. The mask coating 56 minimizes the convective cooling effects of the blood pool upon the regions of the electrode segment 80 that are exposed to it. The temperature condition sensed by the element 80 facing tissue is thereby more accurate. When more than two temperature sensors 80 are used on a given electrode segment 30, masking becomes less advisable, as it reduces the effective surface of the electrode segment 30 available for tissue contact and ablation.

The temperature sensing elements 80 can comprise thermistors or thermocouples. When using thermocouples as the sensing elements 80, a reference or cold junction thermocouple must be employed, which is exposed to a known temperature condition. The reference thermocouple can be placed within the temperature processing element itself. Alternatively, the reference thermocouple can be placed within the handle 18 of the catheter probe 14.

Further details regarding the use of thermocouples can be found in a publication available from Omega, entitled Temperature, pages T-7 to T-18. Furthermore, details of the use of multiple thermocouples as temperature sensing elements 80 in tissue ablation can be found in copending patent application Ser. No. 08/286,930, filed on the same date as this application, entitled "Systems and Methods for Controlling Tissue Ablation Using Multiple Temperature Sensing Elements."

The sensing element or elements 80 can be attached on or near the segmented electrodes 30 in various way.

Figure 23:
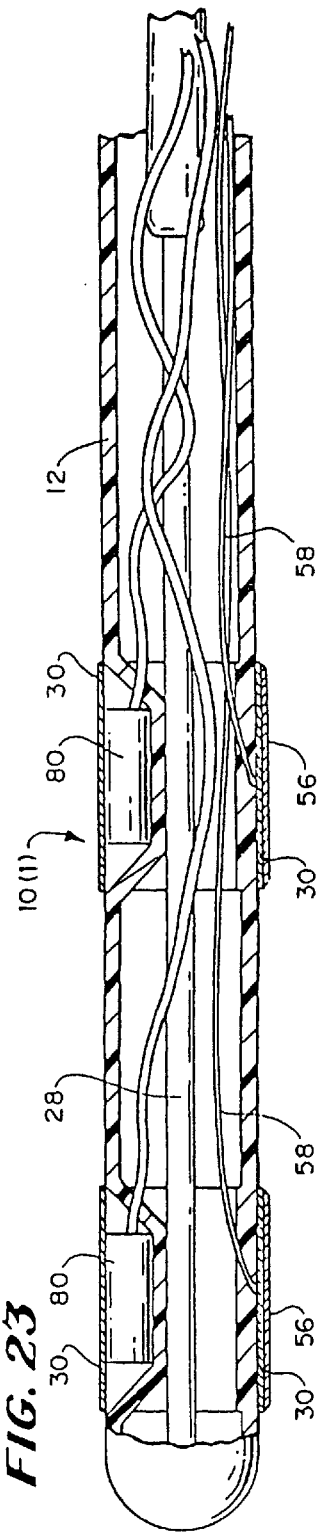
FIG. 23 is a side section view of a flexible ablating element comprising multiple rigid electrode elements, showing one manner of mounting at least one temperature sensing element beneath the electrode elements.

For example, as FIG. 23 shows for the element 10(1), each sensing element 80 is sandwiched between the exterior of the flexible body 32 and the underside of the associated rigid electrode segment 30. In the illustrated embodiment, the sensing elements 80 comprise thermistors. The body 32 is flexible enough to fit the sensing element 80 beneath the electrode segment 30. The plastic memory of the body 32 maintains sufficient pressure against the temperature sensing element 80 to establish good thermal conductive contact between it and the electrode segment 30.

Figure 24:
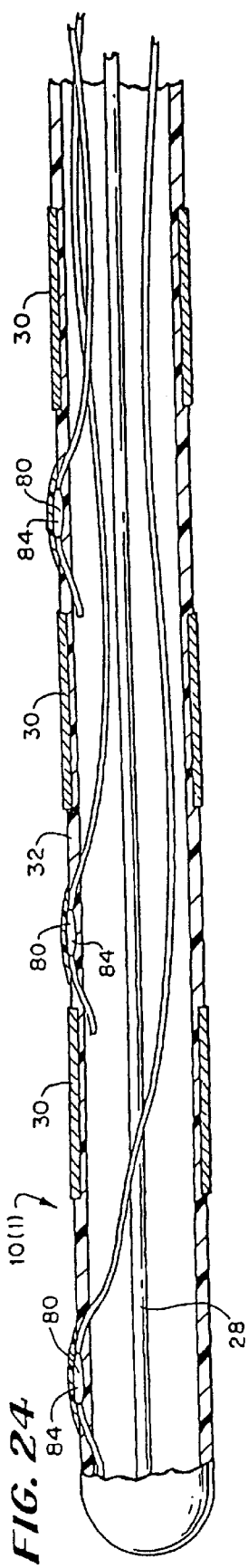
FIG. 24 is a side section view of a flexible ablating element comprising multiple rigid electrode elements, showing another manner of mounting at least one temperature sensing element between adjacent electrode elements.

In an alternative embodiment (as FIG. 24 shows), the temperature sensing element 80 is located between adjacent electrode segments 30. In this arrangement, each sensing element 80 is threaded through the flexible body 32 between adjacent electrode segments 30. In the illustrated embodiment, the temperature sensing elements 80 comprise thermocouples. When the sensing element 80 comprises a thermocouple, an epoxy material 46, such as Master Bond Polymer System EP32HT (Master Bond Inc., Hackensack, N.J.), encapsulates the thermocouple junction 84, securing it to the flexible body 32. Alternatively, the thermocouple junction 84 can be coated in a thin layer of polytetrafluoroethylene (PTFE) material. When used in thicknesses of less than about 0.002 inch, these materials have the sufficient insulating properties to electrically insulate the thermocouple junction 84 from the associated electrode segment 30, while providing sufficient thermally conducting properties to establish thermal conductive contact with electrode segment 30. The use of such materials typically will not be necessary when thermistors are used, because conventional thermistors are already encapsulated in an electrically insulating and thermally conducting material.

Figure 25:
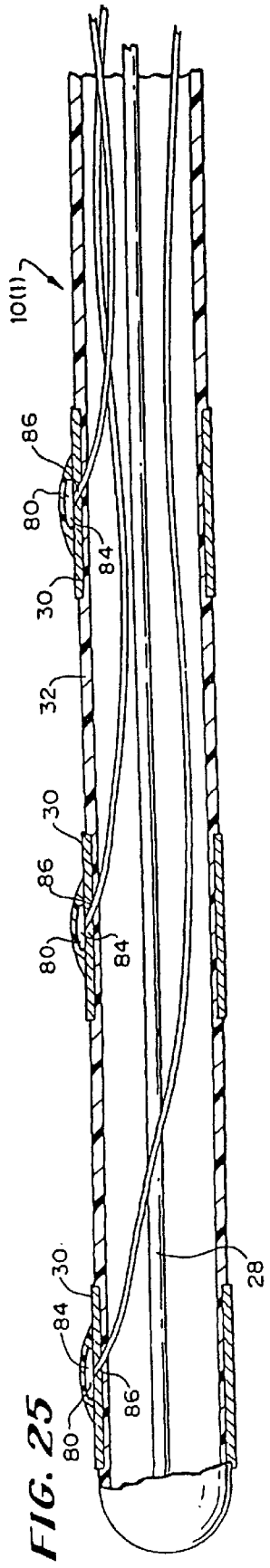
FIG. 25 is a side section view of a flexible ablating element comprising multiple rigid ablating elements, showing another manner of mounting at least one temperature sensing element on the electrode elements.
Figure 26:
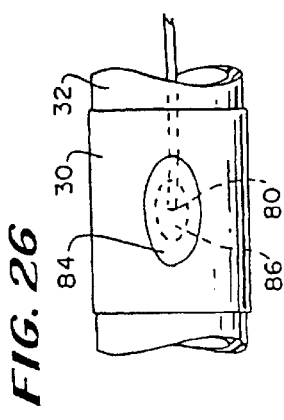
FIG. 26 is an enlarged top view of the mounting the temperature sensing element on the rigid electrode shown in FIG. 26.

In another alternative embodiment (as FIGS. 25 and 26 show), the temperature sensing element 80 physically projects through an opening 86 in each electrode segment 30. As in the embodiment shown in FIG. 24, the sensing elements 80 comprise thermocouples, and a thermally conducting and electrically insulating epoxy material encapsulates the thermocouple junction 84, securing it within the opening 86.

It should be appreciated that some sensing elements 80 can be carried by the electrode segments 30, while other sensing elements 80 can be carried between the element segments 30. Many combinations of sensing element locations are possible, depending upon particular requirements of the ablating procedure.

In the element 10(2) (see FIG. 27), each electrode segment 34 and 36 carries at least one temperature sensing element 80. In the illustrated embodiment, the sensing element 80 comprises a thermistor.

The tip electrode segment 34 carries a temperature sensing element 80 within a cavity 88 drilled along its axis. The body electrode segment 36 also carries at least one temperature sensing element 80, which is sandwiched beneath the electrode segment 36 and the flexible body 38, in the manner previously described and shown in FIG. 23. The sensing element 80 in the electrode segment 36 can be alternatively secured in the manners previously described and shown in FIGS. 24 and 25. Alternatively, as earlier described, the side of the electrode segment 36 opposite to the single sensing temperature element 80 can carrying the mask coating. 56.

Figure 28:
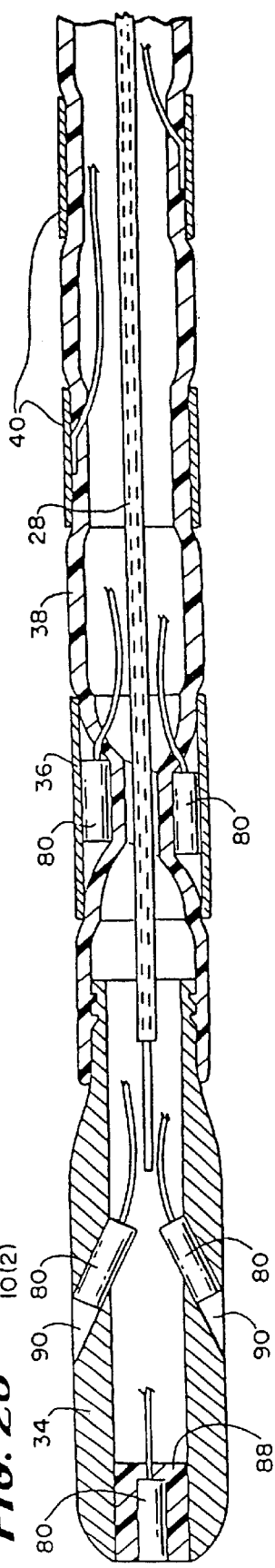

As shown in FIG. 28, either or both electrodes 34 and 36 of element 10(2) can carry more than one temperature sensing element 80. In this arrangement, the tip electrode 34 carries additional temperature sensing elements 80 in side cavities 90. that extend at angles radially from the axis of the electrode 34. The body electrode segment 36 carries additional sensing elements 80 in the manner shown. in FIGS. 21 and 22.

As the diameter of the electrodes 34 and 36 increases, the use of multiple temperature sensing elements 80 becomes more preferred. The multiple sensing elements 80 are circumferentially spaced to assure that at least one element 80 is in thermal conductive contact with the same tissue area as the associated electrode 34 or 36.

(ii) Temperature Sensing with Flexible Electrode Elements

Figure 29:
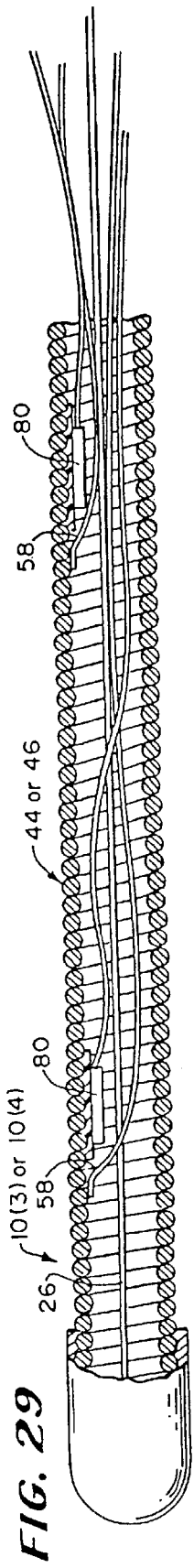
FIG. 29 is a view of a flexible ablating element comprising a continuous wrapped coil, showing one manner of mounting temperature sensing elements along the length of the coil.
Figure 30:
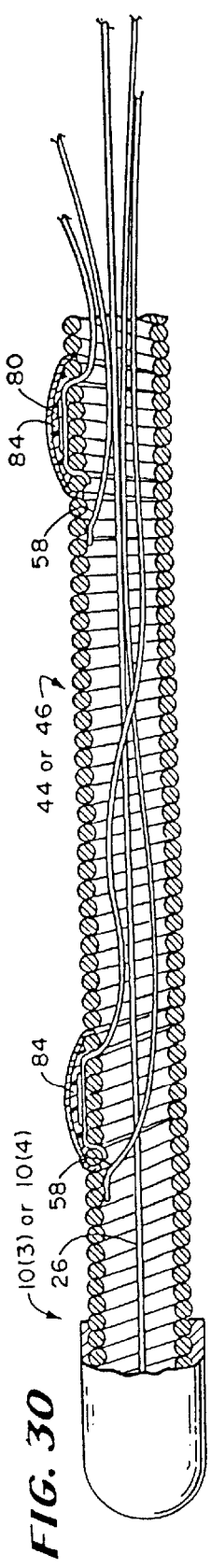
FIG. 30 is a view of a flexible ablating element comprising a continuous wrapped coil, showing another manner of mounting temperature sensing elements along the length of the coil.

In the flexible electrode elements 10(3) and 10(4) (earlier shown in FIGS. 6 and 10), the multiple temperature sensing elements 80 are preferably located at or near the electrical connection points between the wires 58 and the coil electrode segments 44 or continuous coil electrode 46, as FIGS. 29 and 30 best show. This location for the temperature sensing elements 80 is preferred because higher temperatures are typically encountered at these connection points along the coil electrode 44 or 46.

As FIG. 29 shows, the sensing elements 80 can be secured to the inside surface of the coil electrode 44 or 46. Alternatively, the sensing elements 80 can be sandwiched between the inside surface of the electrode 44 or 46 and an underlying flexible body, as FIGS. 15A/B show. In FIGS. 15A/B and 29, the sensing elements 80 comprise thermistors.

Figure 31:
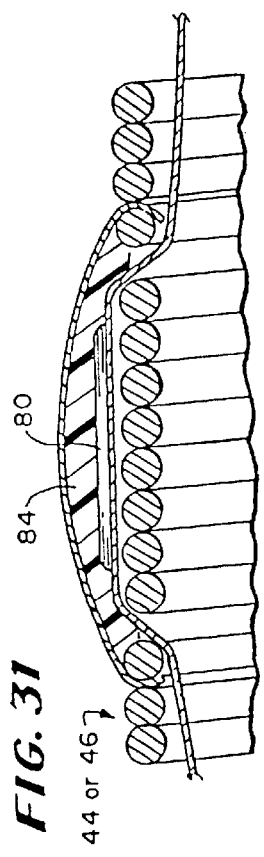
FIG. 31 is an enlarged view of the mounting of the temperature sensing element on the coil electrode shown in FIG. 30.

Alternatively, as FIGS. 30 and 31 show, the sensing elements 80 can be threaded up through the windings in the coil electrode 44 or 46 to lay upon its exterior surface. In the illustrated embodiment, the sensing elements 80 comprise thermocouples, and the thermocouple junction 84 is encapsulated in on an epoxy or PTFE coating, as previously described.

Figure 12A:
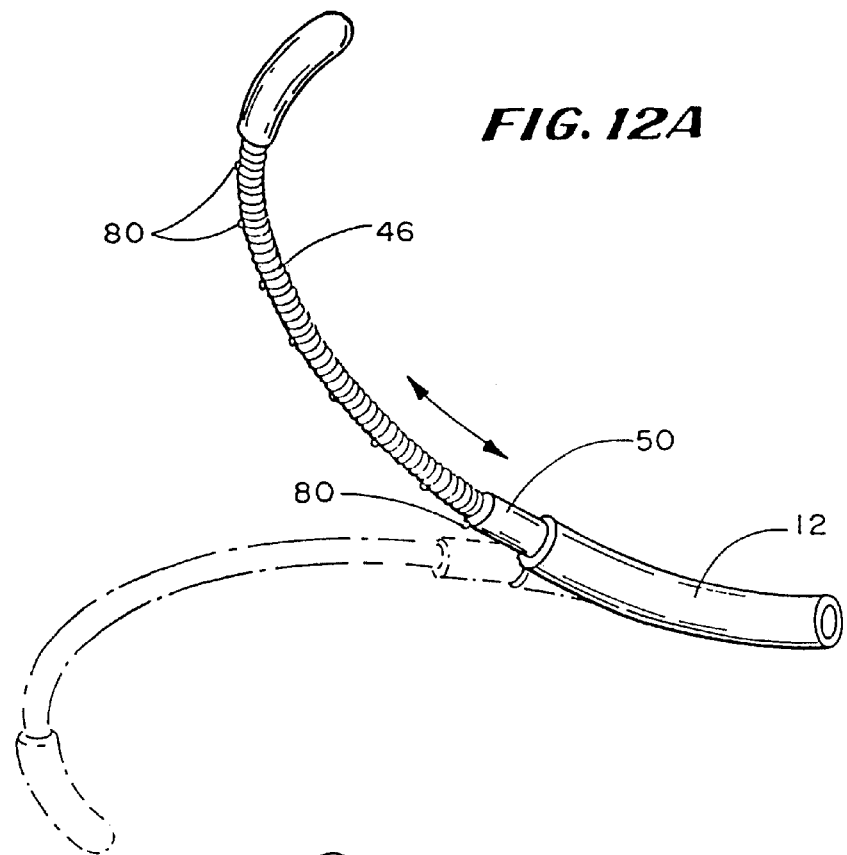
FIGS. 12A/B are views of a flexible ablating element comprising a wrapped wire coil including a movable sheath for changing the impedance of the coil and the ablating surface area when in use.
Figure 12B:
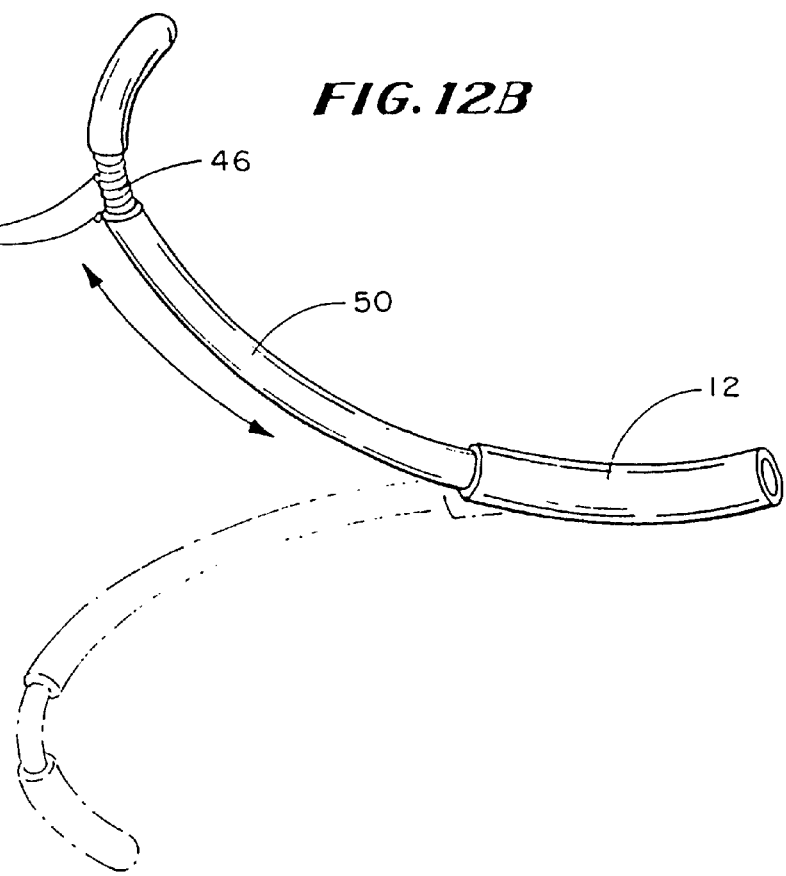

When the elongated electrode 46 includes a sliding sheath 50 see FIGS. 12A/B), the movable sheath 50 carries, in addition to the temperature sensing elements 80 spaced along the length of the coil electrode 56, another temperature sensing element 80 at its distal end.

In the case of flexible electrode element 10(5) (earlier shown in FIG. 11), the sensing elements 80 are sandwiched between the wrapped ribbon 52 and the underlying flexible body 54, as FIG. 32 shows. In the illustrated embodiment, the sensing elements 80 comprise thermocouples having junctions 84 encapsulated in an electrically insulating and thermally conducting coating.

The various shaped electrode structures 64, 68, and 72 (see FIGS. 17A/B; 18A/B; and 19A/B/C, respectively), can also carry multiple temperature sensing elements 80 secured at spaced intervals along the shaped structure, as these Figures show.

An external temperature processing element (not shown) receives and analyses the signals from the multiple temperature sensing elements 80 in prescribed ways to govern the application of ablating energy to the flexible ablating element 10.

The ablating energy is applied to maintain generally uniform temperature conditions along the length of the element.

When the element 10 carries segmented electrode structures, each having more than one sensing element 80, the controller selects the sensing element 80 having the most intimate contact with tissue by selecting among the sensed temperatures the highest sensed temperature. The temperature sensing element 80 providing the highest sensed temperature for a given electrode segment 30 is the one in most intimate contact with heart tissue. The lower sensed temperatures of the other sensing elements 80 on the given electrode segment 30 indicate that the other sensing elements 80 are not in such intimate contact, and are instead exposed to convective cooling in the blood pool.

Further details of the use of temperature sensing in tissue ablation can be found in copending patent application Ser.

No. 08/037,740, filed Mar. 3, 1993, and entitled "Electrode and Associated Systems Using Thermally Insulated Temperature Sensing Elements." Also, further details of the use of multiple temperature sensing elements in tissue ablation can be found in copending patent application Ser. No. 08/286,930 filed. on the same date as this application, entitled "Systems and Methods for Controlling Tissue Ablation Using Multiple Temperature Sensing Elements."

Various features of the invention are set forth in the following claims.

We claim:

1. A device for ablating body tissue comprising a support element having a curved region to peripherally contact a tissue area, and at least two energy emitting zones on the curved region mutually separated across the contacted tissue area, the mutual separation between the zones across the contacted tissue area creating, when the zones simultaneously emit energy, an additive heating effect to form a continuous lesion pattern in the contacted tissue area that spans across the contacted tissue area.

2. A device as claimed in claim 1, wherein each of the electrodes defines a length and a diameter and the length of each electrode is less than or equal to about 5 times its diameter.

3. A device as claimed in claim 1, wherein each of the electrodes defines a length and a diameter and the curvature of the curved region is such that the distance between the electrodes across the tissue area is equal to or less than about 7 times the diameter of at least one of the electrodes.

4. A device as claimed in claim 3, the length of each electrode is less than or equal to about 5 times its diameter.

5. A device as claimed in claim 3, wherein the curvature of the curved region is such that the distance between the electrodes across the tissue area is equal to or less than about 5 times the diameter of at least one of the electrodes.

6. A device as claimed in claim 1, wherein each of the electrodes defines a length and a diameter and the distance between the electrodes across the tissue area is equal to or less than about 4 times the length of at least one of the electrodes.

7. A device as claimed in claim 6, the length of each electrode is less than or equal to about 5 times its diameter.

8. A device as claimed in claim 6, wherein the curvature of the curved region is such that the distance between the electrodes across the tissue area is equal to or less than about 3 times the length of at least one of the electrodes.

9. A device as claimed in claim 1, further comprising:

at least a third electrode on the curved region of the catheter body between the at least two spaced electrodes.

10. A device as claimed in claim 1, further comprising:

at least a third electrode on the catheter body.

11. A device as claimed in claim 1, wherein the curved region defines an arc of about 360 degrees, the at least two electrodes comprise a plurality of electrode pairs, and the electrodes within each pair are separated by an arc of about 180 degrees.

* * * * *

UNITED STATES PATENT AND TRADEMARK OFFICE
CERTIFICATE OF CORRECTION

PATENT NO.     : 6,514,246 B1
DATED          : February 4, 2003
INVENTOR(S)    : David K. Swanson et al.

It is certified that error appears in the above-identified patent and that said Letters Patent is hereby corrected as shown below:

<u>Title page,</u>
Item [75], Inventors, add the following names to the end of the list of inventors:
-- ; Dorin Panescu, Sunnyvale, CA (US); James G. Whayne, Saratoga, CA (US) --

Signed and Sealed this

Fifth Day of August, 2003

JAMES E. ROGAN
*Director of the United States Patent and Trademark Office*